United States Patent
Haselkorn et al.

(10) Patent No.: US 6,682,918 B1
(45) Date of Patent: *Jan. 27, 2004

(54) BACTERIAL SUCROSE SYNTHASE COMPOSITIONS AND METHODS OF USE

(75) Inventors: Robert Haselkorn, Chicago, IL (US); William J. Buikema, Richton Park, IL (US); Christopher C. Bauer, Houston, TX (US)

(73) Assignee: Arch Development Corporation, Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1068 days.

(21) Appl. No.: 08/684,005

(22) Filed: Jul. 19, 1996

(51) Int. Cl.[7] .................................................. C12N 9/10
(52) U.S. Cl. ...................................................... 435/193
(58) Field of Search ............................... 536/23.1, 23.2; 435/172.3, 193, 252.3, 252.33, 320.1, 252.2, 325, 419

(56) References Cited

FOREIGN PATENT DOCUMENTS

| DE | 4124537 | 2/1992 |
| WO | WO 94/13802 | 6/1994 |
| WO | Wo 94/28146 | 12/1994 |

OTHER PUBLICATIONS

M. Ghelue et al., "Sucrose Synthase and Enolase Expression in Actinorhizal Nodules of Alnus glutinosa: Comparison with Legume Nodules", Mol. Gen. Genet. 250: 437–446, 1996.*

Genbank entry X92378, Jan. 1997.*

Van Ghelue et al., "Sucrose Synthase and enolase expression in actinorhizal nodules of *Alnus glutinosa*: comparison with legume nodules," *Molecular and General Genetics*, 250:437–446, 1996.

Amor, Y., et al., "A membrane–associated form of sucrose synthase and its potential role in synthesis of cellulose and callose in plants", Proc. Natl. Acad. Sci. USA, 92:9353–9357 (Sep., 1995).

Arai, M., et al., "Expression of the Gene for Sucrose Synthase during Growth of Mung Bean Seedlings", Plant Cell Physiol., 33(4): 503–506 (1992).

Bauer, C.C., "Isolation and Characterization of Genes Involved in Nitrogen Fixation and Heterocyst Cytodifferentiation in *Anabaena* sp. strain PCC 7120", Disserttaion submitted to The University of Chicago, pp. 1–47 (Dec., 1994).

Chopra, S., et al., "Sucrose synthase of Arabidopsis: Genomic Cloning and sequence characterization", Plant Molecular Biology, 18:131–134 (1992).

Chourey, P.S., et al., "Expression of two sucrose synthetase genes in endosperm and seedling cells of maize: evidence of tissue specific polymerization of protomers", Mol. Gen. Genet, 203:251–255 (1986).

Cossar, J.D., et al., "Thioredoxin as a Modulator of Glucose–6–phosphate Dehydrogenase in a $N_2$–Fising Cyanobacterium", Jour. of Gen. Microbiology, 130:991–998 (1984).

Geigenberger, P., et al., "Sucrose synthase catalyses a readily reversible ereaction in vivo in developing potato tubers and other plan tissues", Planta 189:329–339 (1993).

Huang, Ju–Wei, et al., "Complete Structures of Three Rice Sucrose Synthase Isogenes and Differential Regulation of Their Expressions", Biosci. Biotech. Biochem., 60(2),, 233–239 (1996).

Huber, S.C., et al., "Role and Regulation of Sucrose–Phosphate Synthase in Higher Plants", Annu. Rev. Plant Physiol. Plant Mol. Biol., 47:431–44 (1996).

Küster, H., et al., "The Sucrose Synthase Gene is Predominantly Expressed in the Root Nodule Tissue of *Vicia faba*" The American Phytopathological Society MPMI, vol. 6, No. 4, pp. 507–514 (1993).

Martinez de Ilarduya, O., et al., "Sucrose synthase genes in barley cDNA cloning of the Ss2 type and tissue–specific expression of Ss1 and Ss2", FEBS Lett., vol. 320, (2):177–181 (1993).

Salanoubat, M., et al., "Molecular cloning and sequencing of sucrose synthase cDNA from potato (*Solanum tuberosum I.*): preliminary characterization of sucrose synthase mRNA distribution" Gene, 60:47–56 (1987).

Schilling, N., et al., "Cellular Differentiation of Sucrose Metabolism in *Anabaena variabilis*" Z. Naturforsch., 40c, 776–779 (1985).

Sebková , V., et al., "Biochemical, Physiological, and Molecular Characterization of Sucrose Synthase from *Daucus carota*", Plant Physiol. 108:75–83 (1995).

Werr, W., et al., "Structure of the sucrose synthase gene on chromosome 9 of *Zea mays* L.", EMBO J., vol. 4, No. 6, pp.1373–1380 (1985).

Zrenner, R., et al., "Evidence of the crucial role of sucrose synthase for sink strength using transgenic potato plants (*Solanum tuberosum* L.) ", Plant J., 7(1), 97–107 (1995).

* cited by examiner

*Primary Examiner*—Rebecca E. Prouty
(74) *Attorney, Agent, or Firm*—Fulbright & Jaworski L.L.P.

(57) ABSTRACT

The present invention provides isolated and purified polynucleotides that encode bacterial polypeptides that participate in the utilization of sucrose. Isolated bacterial sucrose synthase compositions and methods of use are provided. Processes for altering sucrose synthase activity, altering the starch and/or sucrose content of bacterial and/or plant cells, methods of identifying sucrose synthase-encoding nucleic acid segments, and compositions comprising sucrose synthase peptides and antibodies are also disclosed.

48 Claims, 7 Drawing Sheets

```
     CTACGAAAAATATTAAGCATCTAAACTATAACCACAGTATAAAAAATTGTCTATCTTTAGTTAGAGCCAATAATACCTAGTTGTGATATTCTAAGTAAA
  1  ----+----|----+----|----+----|----+----|----+----|----+----|----+----|----+----|----+----|----+----|
     GATGCTTTTATAATTCGTAGATTGATATTGGTGTCATATTTTAACAGATAGAAATCAATCTCGGTTATTATGGATCAACAGCTATAAGATTCATTT

TAAGAACAAGGTTTGATACAAAGATAAAAACACAGATGAATTTATCTGTGTTTTTTGCATTGTAGGTGTTGAGATTCTAGGTTGTTAGCCTACG
 101 ----+----|----+----|----+----|----+----|----+----|----+----|----+----|----+----|----+----|----+----|
     ATTCTTGTTCCAAACTATGTTTCTATTTTTGTGTCTATCTACTTAAATAGACACAAAAAAACGTAAACATCCACAACTCTAAGATCAACAATCGGATGC

TTACCCTAGAAAGCAAATAGGTTCAATCTTCCTTCATTTAAGGGGTGAATATGTCAGAATTGATGCAAGCGATTTTAGATAGTGAAGAAAAACATGATTT
 201 ----+----|----+----|----+----|----+----|----+----|----+----|----+----|----+----|----+----|----+----|
     AATGGGATCTTTCGTTTATCCAAGTTAGAAGGAAGTAAATTCCCACTTATACAGTCTTAACTACGTTCGCTAAATCTATCAGTTCTTTTTGTACTAAA

GCGTGGATTTATTAGTGAGTTGCGTCAGCAAGATAAAAATTACCTGCTACGCAACGATATACTGAATGTGTATGCTGAATACTGCTCTAAGTGCCAGAAA
 301 ----+----|----+----|----+----|----+----|----+----|----+----|----+----|----+----|----+----|----+----|
     CGCACCTAAATAATCACTCAACGCAGTCGTTCTATTTTAATGGACGATGCGTTGCTATATGACTTACACATACGACTTATGACGAGATTCACGGTCTTT

CCGGAAACTTCTTATAAGTTTTCTAATCTAAGTAAACTTATTTACTACACTCAAGAATAATTCAAGAAGATTCCAATTTTTGCTTCATTATTCGTCCTA
 401 ----+----|----+----|----+----|----+----|----+----|----+----|----+----|----+----|----+----|----+----|
     GGCCTTTGAAGAATATTCAAAAGATTAGATTCATTTGAATAAATGATGTGAGTTCTTATTAAGTTCTTCTAAGGTTAAAACGAAGTAATAAGCAGGAT
```

FIG. 1A

```
     AGATTGCTGCTCAAGAGGTATATCGACTCACCGCAGATTTAGATGTGGAGCCGATGACTGTGCAGGAATTGTTGGATCTGTGCGGATCGCCTAGTTAATAA
501  ----+----|----+----|----+----|----+----|----+----|----+----|----+----|----+----|----+----|----+----|
     TCTAACGACGAGTTCTCCATATAGCTGAGTGGCGTCTAAATCTACACCTCGGCTACTGACACGTCCTTAACAACCTAGAGACGCGCTAGCGGATCAATTATT

ATTCCATCCTTATGAAGGCGATATATTAGAACTAGATTTCGGCCCCTTCTACGATTACACCCCAACCATCCCGCGATCCCAAGAATATTGGCAAGGGTGTA
601  ----+----|----+----|----+----|----+----|----+----|----+----|----+----|----+----|----+----|----+----|
     TAAGGTAGGAATACTTCCGCTATATAATCTTGATCTAAAGCCGGGGAAGATGCTAATGTGGGGTTGGTAGGCGCTAGGGTTCTTATAACCGTTCCCACAT

CAATATCTCAACGGTTATCTCTCCAGTAAACTTTTTCAAGACTCGGCAACAATGGCTGGAAAGTCTGTTAATTTCTTGGCCTACATAATTACAATGGTA
701  ----+----|----+----|----+----|----+----|----+----|----+----|----+----|----+----|----+----|----+----|
     GTTATAGAGTTGGCAATAGAGAGGTCATTTGAAGAAAAGTTCTGAGCGTTGTTACCGACCTTTCAGACAAATTAAAGAACGCGGATGTATTAATGTTACCAT

TTCAACTACTAATAAACCATCAAATTCAATCACAGCAACAATTATCACAGCAAGTTAAAAACGCGCTTAACTTTGTGAGCGATCGCCCCAATGATGAACC
801  ----+----|----+----|----+----|----+----|----+----|----+----|----+----|----+----|----+----|----+----|
     AAGTTGATGATTATTTGGTAGTTTAAGTTAGTGTCGTTGTTAATAGTGTCGTTCAATTTTGCGCGAATTGAAACACTCGCTAGCGGGGTTACTACTTGG

CTACGAACAATTCCGGCTGCAACTACAAACTATGGGGTTTTGAGCCGGGGTGGGGTAATACAGCTTCTCGTGTGCGGGATACCTTAAACATTTTGGATGAA
901  ----+----|----+----|----+----|----+----|----+----|----+----|----+----|----+----|----+----|----+----|
     GATGCTTGTTAAGGCCGACGTTGATGTTTGATACCCAAACTCGGCCCACCCCATTATGTCGAAGAGCACACGCCCTATGGAATTTGTAAAACCTACTT
```

FIG. 1B

```
      TTGATTGACTCTCCGACCCCCAAACCCTGGAAGCTTTTATCTCTCGCATCCCGATGATTTTCAGAATCGTCTTAGTTTCAGCCCACGGTTGGTTCGGAC
1001  ----+----|----+----|----+----|----+----|----+----|----+----|----+----|----+----|----+----|----+----|
      AACTAACTGAGAGGGCTGGGGGTTTGGGACCTTCGAAAATAGAGAGCGTAGGGCTACTAAAAGTCTTAGCAGAATCAAAGTCGGGTGCCAACCAAGCCTG

AAGAGGGGTTTTAGGTGTCGTCCAGATACTGGTGGTCAAGTAGTGTACGTCCTTGACCAAGCTAAGAATTTAGAAAAGCAACTGCAAGAAGATGCCATACT
1101  ----+----|----+----|----+----|----+----|----+----|----+----|----+----|----+----|----+----|----+----|
      TTCTCCCCAAAATCCAGCAGGTCTATGACCACCAGTTCATCACATGCAGGAACTGGTTCGATTCTTAAATCTTTTCGTTGACGTTCTTCTACGGTATGA

TGCAGGTTTAGAGGTATTGAACGTCCAGCCCAAGGTAATTATCCTCACCCGTCTGATTCCTAATAGTGACGGAACGCTTTGTAACCAAAGGTTAGAAAAA
1201  ----+----|----+----|----+----|----+----|----+----|----+----|----+----|----+----|----+----|----+----|
      ACGTCCAAATCTCCATAACTTGCAGGTCGGGTTCCATTAATAGGAGTGGGCAGACTAAGGATTATCACTGCCTTGCGAAACATTGGTTCCAATCTTTT

GTCTACGGTACAGAGAACGCCTGGATTTTGCGTGTACCTCTGCGGGAGTTTAACCCCAAGATGACGCAGAACTGGATTTCTGATTCGAGTTTTGGCCTT
1301  ----+----|----+----|----+----|----+----|----+----|----+----|----+----|----+----|----+----|----+----|
      CAGATGCCATGTCTCTTGCGACCTAAAACGCACATGGAGACGCCCTCAAATTGGGGTTCTACTGCGTCTTGACCTAAAGAGCTAAGCTCAAAACCGGAA

ATCTAGAAAACCTTTGCCATTGACTCAGAAAGAGAATTGTTGGCAGAATTCCAAGGTAGACCAGACTTAATCGTGGGTAATTATACTGACGGAACTTAGT
1401  ----+----|----+----|----+----|----+----|----+----|----+----|----+----|----+----|----+----|----+----|
      TAGATCTTTGGAAACGGTAACTGAGTCTTTTCTCTTAACAACGGTCTTAAGGTTCCATCTGGTCTGAATTAGCACCCATTAATATGACTGCCCTTGAATCA
```

FIG. 1C

```
1501  TGCTTTTCTGTTGACGCGACGGATGAAAGTTACCCAATGCAACATGCTCATGCTTTAGAAAAATCCAAATACTTGTTAGTAACCTCTACTGGCAAGAT
      ----+----|----+----|----+----|----+----|----+----|----+----|----+----|----+----|----+----|----+----|
      ACGAAAAGACAACTGCGCTGCCTACTTTCAATGGGTTACGTTGTAGCGAGTACGAAATCTTTTAGGTTTATGAACAAATCATTGGAGATGACCGTTCTA

1601  TTGGAAGAAAAATATCATTTCTCTTTACAATTCACGGCTGATTTAATAGCTATGAATGCTGCTAACTTGTCATCAGCAGCACCTATCAAGAAATTGTTG
      ----+----|----+----|----+----|----+----|----+----|----+----|----+----|----+----|----+----|----+----|
      AACCTTCTTTTTATAGTAAAGAGAAATGTTAAGTGCCGACTAAATTATCGATACTTACGACGATTGAACGCAGTAGTCGTCGTGGATAGTTCTTAACAAC

1701  GCACACCAGACAGTATAGGGCAGTATGAGTCTTACCATGCTCTTACAAATGCTCGGAACTGTATCATGTGGTCAACGGCATTGAATTATTTAGCCCCAAATT
      ----+----|----+----|----+----|----+----|----+----|----+----|----+----|----+----|----+----|----+----|
      CGTGTGGTCTGTCATATCCCGTCATACTCAGAATGTTACGGCCTTGACTAGTACACCAGTTGCCGTAACTTAATAAATCGGGTTTAA

1801  TAACGTTGTACCGCCTGGTGTGAATGAAAATTCCTACTTTCCCTACACACAAACTCAAAACAGAATAGAAGCGATCGCGATCGCCTAGAGGAAATGCTG
      ----+----|----+----|----+----|----+----|----+----|----+----|----+----|----+----|----+----|----+----|
      ATTGCAACATGGGGACCACACTTACTTTTAAGGATGAAAGGGATGTGTGTTTGAGTTTGTCTATCTTGCGCTAGCGCTAGGCGGATCTCCTTACGAC

1901  TTTACCCTAGAAGATTCTAGCCAAATCTTCGGCGGAAACTCGACGACCCAAATAAGGCGTCCTATTTTCTCAATGGGCGACTTGACCGAATTAAAAACCTCA
      ----+----|----+----|----+----|----+----|----+----|----+----|----+----|----+----|----+----|----+----|
      AAATGGGATCTTCTAAGATCGGTTTGAGAGCCGTTTATTCGCAGGATAAAAGAGTTACCGCGCTGAACTGGCTTAATTTTGGAGT
```

FIG. 1D

```
      CAGGTTTGGCAGAATGCTTTGGTCAAAGTCAAGAATTGCAAGAACGTTGCAACTTAATTTTAGTTGCAGGTAAGCTGCGTATCGAAGAATCAGAAGATAA
2001  ----+----|----+----|----+----|----+----|----+----|----+----|----+----|----+----|----+----|----+----|
      GTCCAAACCGTCTTACGAAACCAGTTTCAGTTCTTAACGTTCTTGCAACGTTGAATTAAAATCAACGTCCATTCGACGCATAGCTTCTTAGTCTTCTATT

CGAAGAAAAAGACGAAATCGTCAAACTTTACCGGATTATTGACGAATACAACCTGCATGGCAAAATTCGCTGGTTAGGTGTGCGCTTATCCAAAAATGAC
2101  ----+----|----+----|----+----|----+----|----+----|----+----|----+----|----+----|----+----|----+----|
      GCTTCTTTTTCTGCTTTAGCAGTTTGAAATGGCCTAATAACTGCTTATGTTGGACGTACCGTTTTAAGCGACCAATCCACACGCGAATAGGTTTTTACTG

TCCGGGTGAAATTTATCGCGTCTCATTTGGCGATCGCCAAGGCATTTTTGTACAGCCAGCATTATTTGAAGCCTTTGGGTTGACAATCCTGGAGTCAATGATTT
2201  ----+----|----+----|----+----|----+----|----+----|----+----|----+----|----+----|----+----|----+----|
      AGGCCCACTTTAAATAGCGCAGTAAACGCTAGCGGTTCCGTAAAACATGTCGGTCGTAATAAACTTCGGAACCAACTGTTAGGACCTCAGTTACTAAA

CCGGATTGCCAACATTTGCTACCCAATTGGGGGGGCCATTGGAGATTATTCAGGATAAGATTAATGGCTTCTACATTAACCCTACTCATCTAGAAGAAAC
2301  ----+----|----+----|----+----|----+----|----+----|----+----|----+----|----+----|----+----|----+----|
      GGCCTAACGGTTGTAAACGATGGTTAAACCCCCGGTAACCTCTAATAAGTCTATTCTAATTACCGAAGATGTAATTGGGATGAGTAGATCTTCTTTG

AGCCACAAAAATTCTTGATTTCGTCACCAAATGCGAACAAAATCCTAACTATTGGAACATAATTTCCGAGAAAGCCATTGACAGAGTATATAGTACATAC
2401  ----+----|----+----|----+----|----+----|----+----|----+----|----+----|----+----|----+----|----+----|
      TCGGTGTTTTAAGAACTAAAGCAGTGGTTTACGCTTGTTTAGGATTGATAACCTGTATTAAAGGCTCTTCGGTAACTGTCTCATATATCATGTATG
```

FIG. 1E

```
2501 ACCTGGAAAATACACACAACTAAGCTGTTAACCTTAGCTCGGATTTACGGCTTCTGGAATTTTACCTCGAAAGAAAAACGCGAAGATTTATTACGCTACC
     ----+----|----+----|----+----|----+----|----+----|----+----|----+----|----+----|----+----|----+----|
     TGGACCTTTTATGTGTGTTGATTCGACAATTGGAATCGAGCCTAAATGCGAAGACCTTCTTTTTGCGCTTCTAAATAATGCGATGG

2601 TTGAGTCCCTGTTCTACTTAATTTACAAGCCCAGAGGGCAACAACTATTAGAACAGCATAAATATCGGTAATTTGTGATTAGTCAATAGTCATTAGTGCC
     ----+----|----+----|----+----|----+----|----+----|----+----|----+----|----+----|----+----|----+----|
     AACTCAGGGACAAGATGAATTAAATGTTCGGGTCTCGGCGTTGTTGATAATCTTGTCGTATTTATAGCCATTAAACACTAATCAGTTATCAGTAATCACGG
```

FIG. 1F
(SEQ ID NO:1)

```
  1  MSELMQAILDSEEKHDLRGFISELRQQDKNYLLRNDILNVYAEYCSKCQKPETSYKFSNLSKLIYTQEIIQEDSNFCFI
 81  IRPKIAAQEVYRLTADLDVEPMTVQELLDLRORLVNKFHPYEGDILELDFGPFYDYTPTIRDPKNIGKGVQYLNRYLSSK
161  LFQDSQQWLESLFNFLRLHNYNGIQLLINHQIQSQQQLSQQVKNALNFVSDRPNDEPYEQFRLQLQTMGFEPGWGNTASR
241  VRDTLNILDELIDSPDPQTLEAFISRIPMIFRIVLVSAHGWFGQEGVLGRPDTGGQVVYVLDQAKNLEKQLQEDAILAGL
321  EVLNVQPKVIILTRLIPNSDGTLCNQRLEKVYGTENAWILRVPLREFNPKMTQNWISRFEFWPYLETFAIDSERELLAEF
401  QGRPDLIVGNYTDGNLVAFLLTRRMKVTQCNIAHALEKSKYLFSNLYWQDLEEKYHFSLQFTADLIAMNAANFVISSTYQ
481  EIVGTPDSIGQYESYKCFTMPELYHVVNGIELFSPKFNVVPPGVNENSYFPYTQTQNRIESDRDRLEEMLFTLEDSSQIF
561  GKLDDPNKRPIFSMARLDRIKNLTGLAECFGQSQELQERCNLILVAGKLRIEESEDNEEKDEIVKLYRIIDEYNLHGKIR
641  WLGVRLSKNDSGEIYRVICDRQGIFVQPALFEAFGLTILESMISGLPTFATQFGGPLEIIQDKINGFYINPTHLEETATK
721  ILDFVTKCEQNPNYWNIISEKAIDRVVYSTYTWKIHTTKLLTLARIYGFWNFTSKEKREDLLRYLESLFYLIYKPRAQQLL
801  EQHKYR    806
```

FIG. 2

(SEQ ID NO:2)

BACTERIAL SUCROSE SYNTHASE COMPOSITIONS AND METHODS OF USE

The United States government has certain rights in the present invention pursuant to Grant Number GM2 1823 from the National Institutes of Health.

1. BACKGROUND OF THE INVENTION

1.1 Field of the Invention

The present invention relates to the field of molecular biology. More specifically, it concerns nucleic acid compositions comprising bacterial sucrose synthases, methods for making and using native and recombinant sucrose synthase-encoding polypeptides, and methods for making and using polynucleotides encoding sucrose synthase polypeptides.

1.2 Description of the Related Art

1.2.1 Sucrose Synthase

Sucrose synthase (EC 2.1.4.13) is an enzyme that is found in plants and cyanobacteria. It catalyzes the reversible reaction:

UDP-glucose+fructose⇌sucrose+UDP

In plants, sucrose synthase is mostly active in sink tissues such as tubers, seeds, fruits and meristems where it catalyzes the breakdown of phloem-transported sucrose from the leaves to UDP-glucose and fructose. Subsequent reactions in storage tissues utilize the UDP-glucose directly to generate starch using the enzyme UDP-glucose pyrophosphorylase. In other sink tissues, the monosaccharides may accumulate (fruits) or be utilized for energy or growth (roots, meristems). Multiple sucrose synthase alleles have been identified in several plants, and typically display tissue-specific expression (Huang et al., 1996; Choury et al., 1986). Expression levels of sucrose synthase in sink tissues is thought to be the main indicator of sink strength (Amor et al., 1995; Zrenner et al., 1995).

Regulation of sucrose synthase appears to be active at several levels, including transcriptional control, feedback inhibition by glucose and fructose, and transcriptional mechanisms (Geigenberger and Stitt, 1993). Regarding the latter, it has recently been determined that sucrose synthase in maize is reversibly phosphorylated at a serine residue near the N-terminus of the protein, and this site is strongly conserved among all the plant sequences. Similarly sucrose phosphate synthase has also been shown to be controlled by phosphorylation at several serine residues (Huber and Huber, 1996).

1.2.2 Sucrose Phosphate Synthase

Formation of sucrose in source tissues, such as mature leaves, utilizes a different enzyme, sucrose-phosphate synthase (EC 2.4.1.14), which catalyzes the reaction:

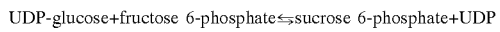

UDP-glucose+fructose 6-phosphate⇌sucrose 6-phosphate+UDP

A subsequent step catalyzed by sucrose phosphatase (EC 3.1.3.24) removes the phosphate from sucrose 6phosphate, essentially making this reaction irreversible. The sucrose is then transported into the phloem of the plant utilizing a sucrose-proton symporter.

1.2.3 Bacterial Sucrose Synthase Differs From the Plant Enzyme

In the filamentous cyanobacterium Anabaena sp. strain PCC 7120 there is evidence that sucrose is synthesized in vegetative cells and is transported to special differentiated cells called heterocysts, where it supports nitrogen fixation. This evidence is based on observations of a sucrose synthase activity in crude extracts that co-purifies with vegetative cells but not heterocysts (Schilling and Ehrnsperger, 1985). An alkaline invertase activity (for the degradation of sucrose) has been identified which copurifies with heterocysts but not vegetative cells. This work suggests that sucrose synthase is responsible for the synthesis of sucrose that is then transported into the heterocyst where it is degraded to glucose and fructose by alkaline invertase. While the role of sucrose synthase in most plant tissues is the breakdown of sucrose, the enzyme has been demonstrated to be freely reversible (Geigenberger and Stitt, 1993), and may function in the synthesis of sucrose in cyanobacteria.

1.2.4 Deficiencies in the Prior Art

The genetic transformation of important commercial agricultural crops with DNA segments encoding sucrose synthase enzymes would be a revolution in the farming of such grains as wheat, rice, maize, barley, rye, and oats. Moreover the availability for modulating the starch and/or sucrose content in plants such as potatoes, tomatoes, fruits such as apples, cherries, pears, strawberries and raspberries would be highly desirable. The ability to modulate nitrogen fixation activity in plants such as soybean, alfalfa, beans, peas, and related legumes would also represent a breakthrough in the areas of improving crop yields where fixed-nitrogen fertilizer input is limited.

Therefore, what is needed in the art are compositions comprising bacterial sucrose synthase-encoding DNA segments and sucrose synthase polypeptides, as well as methods for the alteration of sucrose synthase activity in vitro and in vivo. Methods of identifying and assaying the levels of sucrose synthase activity in plants, fungi, bacteria and cyanobacteria would also be important in genetically engineering cells for altered sucrose and starch production and nitrogen fixation activity.

Moreover, what is lacking in the prior art is the identification of DNA segments encoding bacterial and, particularly, cyanobacterial sucrose synthase enzymes, and the development of methods and processes for their use in creation of modified, transgenic plants which have altered sucrose synthase activity. Moreover, novel methods providing transgenic plants using DNA segments encoding sucrose synthase polypeptides to modulate starch and sucrose biosynthesis in general, and nitrogen fixation activity of cells in specific, are greatly needed to provide transformed plants altered in such activities. Methods for determining sucrose synthase activity in vivo and quantitating the level of sucrose synthase expression in bacteria and transformed plants would also represent major improvements over the current state of the art.

2. SUMMARY OF THE INVENTION

The present invention seeks to overcome these and other inherent deficiencies in the prior art by providing compositions comprising novel sucrose synthase polypeptides from bacterial, and particularly, cyanobacterial species. The invention also provides novel DNA segments encoding prokaryotic sucrose synthases, and methods and processes for their use in regulating the starch and/or sucrose content of plant tissues, for conferring and modulating nitrogen fixation activity in a variety of different cell types, and for altering the activity of sucrose synthase in plant cells in vivo. Also disclosed are methods for determining sucrose synthase activity and expression, and kits for identifying the presence of sucrose synthase polypeptides and DNA segments which encode them.

The bacterial sequences of the present invention differ markedly from eukaryotic enzymes which catalyze the same reaction in higher organisms such as plants. The bacterial proteins disclosed herein have less than 44% sequence homology on average to the eukaryotic proteins, and the nucleic acid sequences encoding the bacterial enzymes are less than 56% identical to plant cDNAs encoding eukaryotic sucrose synthase proteins. The longest contiguous nucleic acid sequence which is identical to any of the sequences in the prior art encoding sucrose synthases is less than 14 residues, suggesting broad differences exist between the novel sequences disclosed herein, and the eukaryotic sequences disclosed in the prior art.

Dramatic differences between prokaryotic and eukaryotic sucrose synthases have been identified by the present inventors in the protein sequences, particularly in the amino terminal region of the proteins. In plants, it has been demonstrated that significant protein homologies exist between plant proteins presumably since the region is a site for protein phosphorylation in eukaryotic species. In sharp contrast, no such phosphorylation site is observed in the prokaryotic sequences disclosed herein, and little amino acid identity is observed. In fact, in the first 20 amino acid residues, virtually no similarity exists to any plant-derived protein.

2.1 Sucrose Synthase Genes and Polynucleotides

The present invention provides polynucleotides and polypeptides relating to a whole or a portion of sucrose synthase of a bacterium, and particularly, the sucrose synthase of a cyanobacterium, as well as processes for making, using, detecting and modulating those polynucleotides and polypeptides.

As used herein the term "polynucleotide" means a sequence of nucleotides connected by phosphodiester linkages. A polynucleotide of the present invention can comprise from about 2 to about several hundred thousand base pairs. Preferably, a polynucleotide comprises from about 5 to about 15,000 base pairs. Preferred lengths of particular polynucleotides are set forth hereinafter.

A polynucleotide of the present invention can be a deoxyribonucleic acid (DNA) molecule or a ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), and uracil (U).

In one embodiment, the present invention contemplates isolated and purified polynucleotides comprising DNA segments encoding polypeptides that comprise a bacterial sucrose synthase. Preferably, the bacterium is a cyanobacterium, and the preferred cyanobacterium is Anabaena. A preferred Anabaena is Anabaena sp. strain PCC 7120.

Preferably, a polypeptide is a sucrose synthase enzyme of a bacterium, and particularly, of a cyanobacterium. This enzyme participates in the biosynthesis of sucrose from UDP-Glucose and fructose. In a preferred embodiment, a sucrose synthase polypeptide is encoded by a polynucleotide comprising a sucA gene (illustrated in FIG. 1A, FIG. 1B, FIG. 1C, FIG. 1D, and FIG. 1E) which has the nucleic acid sequence of SEQ ID NO:1 (Anabaena sucA), or functional equivalents thereof. The sucrose synthase polypeptide (illustrated in FIG. 2) preferably comprises the amino acid sequence of SEQ ID NO:2 (Anabaena sucrose synthase), or functional equivalents thereof.

In yet another aspect, the present invention provides an isolated and purified DNA molecule comprising a promoter operatively linked to a coding region that encodes a bacterial sucrose synthase polypeptide, a cyanobacterial sucrose synthase polypeptide, a fungal sucrose synthase polypeptide, or a plant sucrose synthase, which coding region is operatively linked to a transcription-terminating region, whereby said promoter drives the transcription of said coding region.

2.2 Sucrose Synthase Polypeptides and Anti-sucrose Synthase Antibodies

The present invention also provides an isolated and purified sucrose synthase protein of a bacterium, and particularly, of a cyanobacterium such as Anabaena, which protein includes the 806-amino acid residue sequence of SEQ ID NO:2.

The invention further discloses and claims an enzyme composition, free from total cells, comprising a purified bacterial sucrose synthase that includes a contiguous amino acid sequence from SEQ ID NO:2. Such an enzyme composition has the ability to catalyze the synthesis of sucrose from UDP-glucose and fructose. The composition may include the entire amino acid sequence of SEQ ID NO:2, or alternatively, a peptide derived from the full-length protein. The peptide fragment may comprise from about 15 to about 50 amino acids, or alternatively, comprise larger peptide fragments up to and about 100, 200, 300, 400, 500, 600, 700, or 800 amino acids, even up to and including the 806-amino acid full-length sequence of SEQ ID NO:2. In one embodiment, such as composition may be prepared by the method disclosed herein for producing a bacterial sucrose synthase composition. The protein or peptide may be a wild-type peptide, derived from a wild-type protein by enzymatic, chemical or mechanical means, or alternatively, may be a recombinant protein or peptide.

Another aspect of the invention concerns methods and compositions for the use of the novel peptides of the invention in the production of anti-sucrose synthase antibodies. The present invention also provides methods for identifying sucrose synthase and sucrose synthase-related polypeptides, which methods comprise contacting a sample suspected of containing such polypeptides with an immunologically effective amount of a composition comprising one or more specific anti-sucrose synthase antibodies disclosed herein. Peptides that include the amino acid sequence of SEQ ID NO:2 and epitopic derivatives derived therefrom will be preferred for use in generating such anti-sucrose synthase antibodies. Samples which may be tested or assayed for the presence of such sucrose synthase and sucrose synthase-related polypeptides include whole cells, cell extracts, cell homogenates, cell-free supernatants, and the like. Such cells may be either eukaryotic (such as plant cells) or prokaryotic (such as cyanobacterial and bacterial cells).

In certain aspects, diagnostic reagents comprising the novel peptides of the present invention and/or DNA segments which encode them have proven useful as test reagents for the detection of sucrose synthase and sucrose synthase-related polypeptides.

2.3 Transformation of Plant Cells With sucA DNA

In yet another aspect, the present invention discloses novel transgenic plants containing the DNA segments disclosed herein. Also provided is a process of altering the synthase of sucrose in a cell comprising transforming the cell with a DNA molecule comprising a promoter operatively linked to a coding region that encodes a bacterial sucrose synthase polypeptide having the ability to catalyze the synthesis of sucrose from UDP-glucose and fructose, which coding region is operatively linked to a transcription-terminating region, whereby the promoter is capable of driving the transcription of the coding region in the cell.

Another aspect of the invention relates generally to transgenic plants which express genes or gene segments encoding the novel polypeptide compositions disclosed herein. As used herein, the term "transgenic plants" is intended to refer to plants that have incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression. It is contemplated that in some instances the genome of transgenic plants of the present invention will have been augmented through the stable introduction of the transgene. However, in other instances, the introduced gene will replace an endogenous sequence.

A preferred gene which may be introduced includes, for example, the sucrose synthase DNA sequences from cyanobacterial or bacterial origin, particularly those described herein which are obtained from the cyanobacterial species Anabaena, or from any of those sequences which have been genetically engineered to decrease or increase the activity of the sucrose synthase in such transgenic species.

Vectors, plasmids, cosmids, YACs (yeast artificial chromosomes) and DNA segments for use in transforming such cells will, of course, generally comprise either the DNAs, gene or gene sequences of the present invention, and particularly those encoding sucrose synthase. These DNA constructs can further include structures such as promoters, enhancers, polylinkers, or even regulatory genes as desired. The DNA segment or gene may encode either a native or modified sucrose synthase, which will be expressed in the resultant recombinant cells, and/or which will impart an improved phenotype to the regenerated plant.

2.4 Modulating Starch and Sucrose Content in Plants via Sucrose Synthase Transgenes In other aspects of the present invention, the invention concerns processes of modifying the sucrose and/or starch content of a plant cell. Such modifications generally involve expressing in such plant cells transgenic DNA segments encoding a bacterial, and preferably, a cyanobacterial sucrose synthase composition of the present invention. Such processes would generally result in increased expression of sucrose synthase and hence, increased sucrose production in such cells. Alternatively, when it is desirable to decrease the sucrose production of such cells, sucrose synthase-encoding transgenic DNA segments or antisense (complementary) DNA segments to genomic sucrose synthase-encoding DNA sequences may be used to transform cells.

Either process may be facilitated by introducing into such cells DNA segments encoding a sucrose synthase polypeptide, as long as the resulting transgenic plant expresses the sucrose synthase-encoding transgene.

In an important aspect, the invention discloses and claims a process of altering the sucrose content in a eukaryotic cell comprising transforming the cell with a DNA molecule comprising a promoter operatively linked to a coding region that encodes a prokaryotic sucrose synthase polypeptide. The promoter must be capable of driving the transcription of the sucA coding region in the cell, and in one embodiment, the coding region may also be operatively linked to a transcription-terminating region. A transformed cell produced in accordance with this process also represents one aspect of the invention.

The present invention also provides a transformed plant produced in accordance with the above process as well as a transgenic plant and a transgenic plant seed having incorporated into its genome a transgene that encodes a sucrose synthase polypeptide having the ability to catalyze the synthesis of sucrose from UDP-glucose and fructose. All such transgenic plants having incorporated into their genome transgenic DNA segments encoding a bacterial, and preferably, a cyanobacterial sucrose synthase polypeptide are aspects of this invention.

2.5 Sucrose Synthase Gene Screening Methods and Immunodetection Kits

In an further embodiment, the invention discloses and claims a method for detecting a nucleic acid sequence encoding a bacterial sucrose synthase polypeptide. The method comprises obtaining sample nucleic acids suspected of encoding a bacterial sucrose synthase, contacting the nucleic acids with an isolated nucleic acid segment encoding a bacterial sucrose synthase under conditions effective to allow hybridization of substantially complementary nucleic acids, and then detecting the hybridized complementary nucleic acids which are formed. The inventors contemplate that the method may be used to analyze nucleic acids which are located within a cell, or alternatively, to analyze nucleic acids which have been separated from a cell prior to contact.

A further object of the invention is a method for detecting a prokaryotic, and in particular, bacterial, sucrose synthase peptide in a biological sample. Such a method generally comprises obtaining a biological sample suspected of containing a bacterial sucrose synthase peptide, contacting the sample with a first antibody that binds to a prokaryotic sucrose synthase protein or peptide under conditions effective to allow the formation of immune complexes, and then detecting the immune complexes which are formed. The presence of such immune complexes are indicative of the presence of such a bacterial sucrose synthase peptide.

In a related embodiment, an immunodetection kit is provided for use in the aforementioned method. This kit generally comprises, in suitable container means, a bacterial sucrose synthase protein or peptide, or a first antibody that binds to a bacterial sucrose synthase protein or peptide, and an immunodetection reagent.

Such a kit can contain a nucleic acid segment or an antibody of the present invention. The kit can contain reagents for detecting an interaction between a sample and a nucleic acid or antibody of the present invention. The provided reagent can be radio-, fluorescently- or enzymatically-labeled. The kit can contain a known radiolabeled agent capable of binding or interacting with a nucleic acid or antibody of the present invention.

The reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media, a test plate having a plurality of wells, or a microscope slide. When the reagent provided is a dry powder, the powder can be reconstituted by the addition of a suitable solvent, that may be provided.

In still further embodiments, the present invention concerns immunodetection methods and associated kits. It is proposed that the sucrose synthase peptides of the present invention may be employed to detect antibodies having reactivity therewith, or, alternatively, antibodies prepared in accordance with the present invention, may be employed to detect sucrose synthase or sucrose synthase-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either a sucrose synthase peptide or a sucrose synthase-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of sucrose synthase or sucrose synthase-related proteins or peptides and/or antibodies in a sample. Samples may include cells, cell supernatants, cell suspensions, cell extracts, enzyme fractions, protein extracts, or other cell-free compositions suspected of containing sucrose synthase peptides. Generally speaking, kits in accordance with the present invention will include a suitable sucrose synthase peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

2.6 ELISAs and Immunoprecipitation

ELISAs may be used in conjunction with the invention. In an ELISA assay, proteins or peptides incorporating sucrose synthase antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hours, at temperatures preferably on the order of about 25° C. to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectra spectrophotometer.

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g. enzyme-substrate pairs.

2.7 Western Blots

The compositions of the present invention will find great use in immunoblot or western blot analysis. The anti-peptide antibodies may be used as high-affinity primary reagents for the identification of proteins immobilized onto a solid support matrix, such as nitrocellulose, nylon or combinations thereof. In conjunction with immuno-precipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

2.8 Epitopic Core Sequences

The present invention is also directed to protein or peptide compositions, free from total cells and other peptides, which comprise a purified protein or peptide which incorporates an epitope that is immunologically cross-reactive with one or more anti-sucrose synthase antibodies.

As used herein, the term "incorporating an epitope(s) that is immunologically cross-reactive with one or more anti-sucrose synthase antibodies" is intended to refer to a peptide or protein antigen which includes a primary, secondary or tertiary structure similar to an epitope located within a sucrose synthase polypeptide. The level of similarity will generally be to such a degree that monoclonal or polyclonal antibodies directed against the sucrose synthase polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of sucrose synthase immunodominant epitopes, and/or their functional equivalents, suitable for use in eliciting an immune response in an animal is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of 8 to 20 amino acids in length, and more preferably about 8 to about 15 amino acids in length. It is proposed that shorter antigenic sucrose synthase-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to sucrose synthase and sucrose synthase-related sequences. These epitopic core sequences are identified herein in particular aspects as hydrophilic regions of the sucrose synthase polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on transferrin-binding protein antibodies. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

2.9 DNA Segments

The present invention also concerns DNA segments, that can be isolated from virtually any source, that are free from total genomic DNA and that encode the novel peptides disclosed herein. DNA segments encoding these peptide species may prove to encode proteins, polypeptides, subunits, functional domains, and the like of sucrose synthase-related or other non-related gene products. In addition these DNA segments may be synthesized entirely in vitro using methods that are well-known to those of skill in the art.

As used herein, the term "DNA segment" refers to a DNA molecule that has been isolated free of total genomic DNA of a particular species. Therefore, a DNA segment encoding a sucrose synthase peptide refers to a DNA segment that contains sucrose synthase coding sequences yet is isolated away from, or purified free from, total genomic DNA of the species from which the DNA segment is obtained. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified sucrose synthase gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes both genomic sequences, cDNA sequences and smaller engineered gene segments that express, or may be adapted to express, proteins, polypeptides or peptides.

"Isolated substantially away from other coding sequences" means that the gene of interest, in this case, a gene encoding sucrose synthase, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode a sucrose synthase peptide species that includes within its amino acid sequence an amino acid sequence essentially as set forth in SEQ ID NO:2.

The term "a sequence essentially as set forth in SEQ ID NO:2" means that the sequence substantially corresponds to a portion of the sequence of SEQ ID NO:2, and has relatively few amino acids that are not identical to, or a biologically functional equivalent of, the amino acids of any of these sequences. The term "biologically functional equivalent" is well understood in the art and is further defined in detail herein (for example, see Illustrative Embodiments). Accordingly, sequences that have between about 70% and about 80%, or more preferably between about 81% and about 90%, or even more preferably between about 91% and about 99% amino acid sequence identity or functional equivalence to the amino acids of SEQ ID NO:2 will be sequences that are "essentially as set forth in SEQ ID NO:2."

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch encoding either of the peptide sequences disclosed in SEQ ID NO:2, or that are identical to or complementary to DNA sequences which encode any of the peptides disclosed in SEQ ID NO:2, and particularly the DNA segment disclosed in SEQ ID NO:1. For example, DNA sequences such as about 14 nucleotides, and that are up to about 13,000, about 5,000, about 3,000, about 2,000, about 1,000, about 500, about 200, about 100, about 50, and about 14 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–1,500; 1,500–2,000; 2,000–2,500; 2,500–2,600, and up to and including the full-length sequence of SEQ ID NO:1, of 2700 nucleotides etc. and the like.

It will also be understood that this invention is not limited to the particular nucleic acid sequences which encode peptides of the present invention, or which encode the amino acid sequence of SEQ ID NO:2, including those DNA sequence which is particularly disclosed in SEQ ID NO:1. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a sucrose synthase peptide in its natural environment. Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the Pichia expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of sucrose synthase peptides or epitopic core regions, such as may be used to generate anti-sucrose synthase antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequence from SEQ ID NO:2.

In addition to their use in directing the expression of sucrose synthase peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment of SEQ ID NO:1 will find particular utility. Longer contiguous identical or complementary sequences, e.g., those of about 20, 30, 40, 50, 100, 200, 500, 1,000, 2,000, etc. (including all intermediate lengths and up to and including the full-length sequence of 2700 nucleotides will also be of use in certain embodiments.

The ability of such nucleic acid probes to specifically hybridize to sucrose synthase-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10–14, 15–20, 30, 50, or even of 100–200 nucleotides or so, identical or complementary to DNA sequence of SEQ ID NO:1 are particularly contemplated as hybridization probes for use in, e.g., Southern and Northern blotting. Smaller fragments will generally find use in hybridization embodiments, wherein the length of the contiguous complementary region may be varied, such as between about 10–14 and about 100 or 200 nucleotides, but larger contiguous complementarity stretches may be used, according to the length complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating sucrose synthase-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1994; Segal 1976; Prokop, 1991; and Kuby, 1994, are particularly relevant.

Of course, for some applications, for example, where one desires to prepare mutants employing a mutant primer strand hybridized to an underlying template or where one seeks to isolate sucrose synthase-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

2.10 Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the codons listed in Table 1.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

2.11 Site-specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M1 3 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

2.12 Antibody Compositions and Methods for Generating an Immune Response

The invention provides a means for generating an immune response in an animal, particularly for the purpose of producing antibodies which are reactive against the novel SucA peptides dislosed herein. The process for generating an immune response in an animal is well-known in the art, but generally comprises administering to an animal a pharmaceutical composition comprising an immunologically effective amount of a bacterial sucrose synthase composition.

A further embodiment of the invention is a purified antibody that binds to a bacterial sucrose synthase protein or peptide. Means for preparing and characterizing antibodies are well known in the art (See, e.g., Harlow and Lane, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified sucrose synthase protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag 4 1, Sp210-Ag14, OF, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, (Gefter et al., 1977). The use of electrically induced fusion methods is also appropriate (Goding, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

3. BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1 is shown on six panels, FIG. 1A, FIG. 1B, FIG. 1C, FIG. 1D, FIG. 1E, and FIG. 1F, and illustrates the complete nucleotide sequence of the sucrose synthase gene, sucA, from Anabaena sp. strain PCC 7120 (SEQ ID NO:1). The deduced amino acid sequence is shown in FIG. 2.

FIG. 2 shows the deduced amino acid sequence of the sucrose synthase gene, sucA, from Anabaena sp. strain PCC 7120 (SEQ ID NO:2). The corresponding nucleotide sequence is shown in FIG. 1A, FIG. 1B, FIG. 1C, FIG. 1D, and FIG. 1E.

4. DESCRIPTION OF ILLUSTRATIVE EMBODIMENTS

4.1 Definitions

The following words and phrases have the meanings set forth below:

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g., plant protoplast or explant).

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. A plasmid is an exemplary vector.

4.2 Probes and Primers

In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected sucrose synthase gene sequence, e.g., a sequence such as that shown in SEQ ID NO:1. The ability of such nucleic acid probes to specifically hybridize to a sucrose synthase gene sequence lend them particular utility in a variety of embodiments. Most importantly, the probes can be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a sucrose synthase gene from a bacterium, a cyanobacterium, a fungus, or a plant using PCR™ technology. Segments of sucrose synthase genes from other organisms may also be amplified by PCR™ using such primers.

To provide certain of the advantages in accordance with the present invention, a preferred nucleic acid sequence employed for hybridization studies or assays includes sequences that are complementary to at least a 14 to 30 or so long nucleotide stretch of a sucrose synthase-encoding sequence, such as that shown in SEQ ID NO:1. A size of at least 14 nucleotides in length helps to ensure that the fragment will be of sufficient length to form a duplex molecule that is both stable and selective. Molecules having complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments may be readily prepared by, for example, directly synthesizing the fragment by chemical means, by application of nucleic acid reproduction technology, such as the PCR™ technology of U.S. Pat. Nos. 4,683,195, and 4,683,202, herein incorporated by reference, or by excising selected DNA fragments from recombinant plasmids containing appropriate inserts and suitable restriction sites.

Accordingly, a nucleotide sequence of the invention can be used for its ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids, for example, one will select relatively low salt and/or high temperature conditions, such as provided by about 0.02 M to about 0.15 M NaCl at temperatures of about 50° C. to about 70° C. These conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate a sucrose synthase coding sequence from a related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

4.3 Expression Vectors

The present invention contemplates an expression vector comprising a polynucleotide of the present invention. Thus, in one embodiment an expression vector is an isolated and purified DNA molecule comprising a promoter operatively linked to an coding region that encodes a polypeptide having the ability to catalyze the carboxylation of a biotin carboxyl carrier protein of a cyanobacterium, which coding region is operatively linked to a transcription-terminating region, whereby the promoter drives the transcription of the coding region.

As used herein, the term "operatively linked" means that a promoter is connected to an coding region in such a way that the transcription of that coding region is controlled and regulated by that promoter. Means for operatively linking a promoter to a coding region are well known in the art.

Where an expression vector of the present invention is to be used to transform a cyanobacterium, a promoter is selected that has the ability to drive and regulate expression in cyanobacteria. Promoters that function in bacteria are well known in the art. An exemplary and preferred promoter for the cyanobacterium Anabaena is the glnA gene promoter. The cyanobacterial sucA gene promoter(s) themselves can also be used.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described (Poszkowski et al., 1989; Odell et al., 1985), and temporally regulated, spatially regulated, and spatio-temporally regulated (Chau et al., 1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, modified CaMV 35S promoters, or tissue-specific or developmentally specific promoters affecting particular plant species in a unique manner.

Where the promoter is a near-constitutive promoter such as CaMV 35S, increases in polypeptide expression are found in a variety of transformed plant tissues (e.g., callus, leaf, seed and root). Alternatively, the effects of transformation can be directed to specific plant tissues by using plant integrating vectors containing a tissue-specific promoter.

An exemplary tissue-specific promoter is the lectin promoter, which is specific for seed tissue. The Lectin protein in soybean seeds is encoded by a single gene (Le1) that is only expressed during seed maturation and accounts for about 2 to about 5% of total seed mRNA. The lectin gene and seed-specific promoter have been fully characterized and used to direct seed specific expression in transgenic tobacco plants (Vodkin et al., 1983; Lindstrom et al., 1990.)

An expression vector containing a coding region that encodes a polypeptide of interest is engineered to be under control of the lectin promoter and that vector is introduced into plants using, for example, a protoplast transformation method (Dhir et al., 1991). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP Carboxylase (Cashmore et al., 1983), Ti plasmid mannopine synthase (Langridge et al., 1989), Ti plasmid nopaline synthase (Langridge et al., 1989), petunia chalcone isomerase (Van Tunen et al., 1988), bean glycine rich protein 1 (Keller et al., 1989), CaMV 35s transcript (Odell et al., 1985) and Potato patatin (Wenzler et al., 1989). Preferred promoters are the cauliflower mosaic virus (CaMV 35S) promoter and the S-E9 small subunit RuBP carboxylase promoter.

The choice of which expression vector and ultimately to which promoter a polypeptide coding region is operatively linked depends directly on the functional. properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of Agrobacterium tumefaciens described (Rogers et al., 1987). However, several other plant integrating vector systems are known to function in plants including pCaMVCN transfer control vector described (Fromm et al., 1985). Plasmid pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin (Kan) resistance; i.e., the chimeric gene containing the nopaline synthase promoter, Tn5 neomycin phosphotransferase II (nptII) and nopaline synthase 3' nontranslated region described (Rogers et al., 1988).

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to catalyze the synthase of sucrose from UDP-Glucose and fructose of a cyanobacterium is preferably a sucrose synthase enzyme of a cyanobacterium. In a preferred embodiment, such a polypeptide has the amino acid residue sequence of SEQ ID NO:2, or a functional equivalent of this sequence. In accordance with such an embodiment, a coding region comprising the DNA sequence of SEQ ID NO:1 is particularly preferred. Such a nucleic acid segment comprises the Anabaena sucA gene.

4.4 Polypeptides

The present invention provides novel polypeptides that define a whole or a portion of a sucrose synthase of a bacterium, and preferably, a cyanobacterium. In one embodiment, thus, the present invention provides an isolated sucrose synthase polypeptide such as the Anabaena SucA protein. Preferably, sucrose synthase protein from Anabaena includes the amino acid sequence of SEQ ID NO:2, with such amino acid sequence listing encoded by the DNA segment of SEQ ID NO:1.

4.5 Transformed or Transgenic Cells or Plants

A cyanobacterium, a yeast cell, or a plant cell or a plant transformed with an expression vector of the present invention is also contemplated. A transgenic cyanobacterium, yeast cell, plant cell or plant derived from such a transformed or transgenic cell is also contemplated. Means for transforming cyanobacteria and yeast cells are well known in the art. Typically, means of transformation are similar to those well known means used to transform other bacteria or yeast such as *E. coli* or *Saccharomyces cerevisiae*.

Methods for DNA transformation of plant cells include Agrobacterium-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as by Agrobacterium infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973; Zatloukal et al., 1992); (2) physical methods such as microinjection (Capecchi, 1980), electroporation (Wong and Neumann, 1982; Fromm et al., 1985) and the gene gun (Johnston and Tang, 1994; Fynan et al., 1993); (3) viral vectors (Clapp, 1993; Lu et al., 1993; Eglitis and Anderson, 1988; Eglitis et al., 1988); and (4) receptor-mediated mechanisms (Curiel et al., 1991; 1992; Wagner et al., 1992).

4.5.1 Electroporation

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation, is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

4.5.2 Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly stably transforming monocots, is that neither the isolation of protoplasts (Cristou et al., 1988) nor the susceptibility to Agrobacterium infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure. Methods for the biolistic transformation of maize and other monocot species are well described in Intl. Pat. Appl. Pub. No. WO 91/02071.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described (Fraley et al., 1985; Rogers et al., 1987). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern Agrobacterium transformation vectors are capable of replication in *E. coli* as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

Agrobacterium-mediated transformation of leaf disks and other tissues such as cotyledons and hypocotyls was once limited to plants that Agrobacterium naturally infects, and for that reason, Agrobacterium-mediated transformation has been most efficient in dicotyledonous plants. However, recent advances in the art has provided methods for transformation of several monocots using Agrobacterium. One such report for asparagus using Agrobacterium vectors has been described (Bytebier et al., 1987), as well as recent publications for wheat (Intl. Pat. Appl. Pub. No. WO 94/0077).

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced carboxylase activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments (see, for example, Potrykus et al., 1985; Lorz et al., 1985; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts are described (Fujimura et al., 1985; Toriyama et al., 1986; Yamada et al., 1986; Abdullah et al., 1986).

To transform plant strains that cannot be successfully regenerated from protoplasts, other ways to introduce DNA into intact cells or tissues can be utilized. For example, regeneration of cereals from immature embryos or explants can be effected as described (Vasil, 1988). In addition, "particle gun" or high-velocity microprojectile technology can be utilized. (Vasil et al., 1992) Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

Thus, the amount of a gene coding for a polypeptide of interest (i.e., a polypeptide having carboxylation activity) can be increased in monocotyledonous plants such as corn by transforming those plants using particle bombardment methods (Maddock et al., 1991). By way of example, an expression vector containing an coding region for a sucrose synthase and an appropriate selectable marker is transformed into a suspension of embryonic maize or wheat cells using a particle gun to deliver the DNA coated on microprojectiles, or alternatively, the DNA is introduced by Agrobacterium-mediated methods. Regardless of the particular method used, transgenic plants may be regenerated from transformed embryonic calli that express sucrose synthase.

DNA can also be introduced into plants by direct DNA transfer into pollen as described (Zhou et al., 1983; Hess, 1987; Luo et al., 1988), or via pollen tubes (Intl. Pat. Appl. Publ. No. WO 93/18168) or ovules (Intl. Pat. Appl. Publ. No. WO 94/00583). Expression of polypeptide coding genes can be obtained by injection of the DNA into reproductive organs of a plant as described (Pena et al., 1987). DNA can also be injected directly into the cells of immature embryos and the rehydration of desiccated embryos as described (Neuhaus et al., 1987; Benbrook et al., 1986).

The development or regeneration of plants from either single plant protoplasts or various explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by Agrobacterium from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants.

A transgenic plant of the present invention containing a desired polypeptide is cultivated using methods well known to one skilled in the art. Any of the transgenic plants of the present invention can be cultivated to isolate the desired sucrose synthase activity. A transgenic plant of this invention thus has an increased amount of a sucrose synthase coding region (e.g., gene) that encodes the polypeptide of interest, and thus, the DNA content of such a transformed (or transgenic) plant has been augmented to include one or more exogenous sucrose synthase genes and one or more 'scorable' or detectable marker genes which may be used to determine the success of the particular transformation method and to permit screening of suitable transgenic cells following such introduction of the exogenous genes. A preferred transgenic plant is an independent segregant and can transmit the transformed gene and, thus, the corresponding activity of that gene to its progeny. A highly preferred transgenic plant is homozygous for that gene, and transmits that gene to all of its offspring on sexual mating.

Another aspect of the present invention is a seed from a transgenic plant produced in accordance with the methods and compositions disclosed herein. Seed from a transgenic plant is grown in the field or greenhouse, and resulting sexually mature transgenic plants are self-pollinated to generate true breeding plants.

Another composition of the present invention comprises a progeny from such a seed composition. The progeny, or offspring, from the transgenic plants disclosed become true breeding lines that are evaluated for, by way of example, herbicide resistance, preferably in the field, under a range of environmental conditions.

The commercial value of a transgenic plant, seed, or progeny thereof, with a bacterial sucrose synthase transgene incorporated into its genome is enhanced if many different hybrid combinations are available for sale. The user typically grows more than one kind of hybrid based on such differences as time to maturity, standability or other agronomic traits. Additionally, hybrids adapted to one part of a country are not necessarily adapted to another part because of differences in such traits as maturity, disease and herbicide resistance. Because of this, sucrose synthase transgenes are preferably bred into a large number of parental lines so that many hybrid combinations can be produced. Methods for such propagation are well-known to skill in the art, and will vary for the particular species so transformed, and the particular application wherein modulated sucrose synthase activity is desired.

4.6 Modification of Starch and Sucrose Content of Plant Cells

Manipulation of the starch and/or sucrose content and quality of seeds may benefit from knowledge of this structure and regulation of the sucA gene.

Genes of the present invention may be introduced into plants, particularly monocotyledonous plants, particularly commercially important grains. A wide range of novel transgenic plants produced in this manner may be envisioned depending on the particular constructs introduced into the transgenic plants. The largest use of grain is for feed or food. Introduction of genes that alter the composition of the grain may greatly enhance the feed or food value.

The introduction of genes encoding sucrose synthase may alter the starch and/or sucrose content of the plant cell, and thus may be of significant value. Increases in starch content may result in increases in metabolizable-energy-content and -density of the seeds for uses in feed and food. The introduction of genes such as sucrose synthase which encode rate-limiting enzymes in starch biosynthesis, or replacement of these genes through gene disruption or deletion mutagenesis could have significant impact on the quality and quantity of sugars present in such transgenic plants.

Likewise, the introduction of the sucrose synthase genes of the present invention may also alter the balance of sugars present in the cells providing a more healthful or nutritive feedstuff. Alternatively, such properties may also be altered to improve the starch content in tubers such as potatoes.

Increased starch content of potato tubers is desirable so as to improve the nutritional value of the food and increase the total yield of starch for specialized foods and industrial uses. It also improves processing of potato products, leading to increased product recovery and reduced oil absorption that results in products with reduced fat content. Such improvements find particular desirability in the potato chip and french fry industries.

Increased sugar concentration in fruits such as tomatoes leads to higher yields of processed product and less energy use for the removal of excess water. The taste of certain fruits may also be improved by increased sugar content.

In another embodiment, the introduction of DNA segments comprising the bacterial sucA gene may lead to alteration of symbiotic nitrogen fixation activity of the transformed plant cells.

Targeting expression of sucrose synthase to the root nodules of legumes and other plants that form nitrogen fixing symbioses may lead to increased fixed nitrogen supplied to the plant thereby resulting in plant products with improved nutritional value, such as a higher protein content. Higher protein content in feedstock plants for animal feed results in lower costs to farmers and results in higher productivity. Higher protein levels in plants for human consumption lead to natural foods having higher nutritional values.

4.7 Subtracted cDNA Libraries

The procedures for producing double-stranded cDNA in eukaryotic cells have been well documented in the literature (Ausubel et al., 1987; Sambrook et al., 1989). In essence, they involve the isolation of mRNA species by running total RNA over an oligo-dT column; elution of the bound mRNA and production of a DNA strand complementary to the mRNA utilizing reverse transcriptase and an oligo-dT primer. Second strand synthesis follows using a DNA polymerase and the resulting double-stranded molecules are ligated with adapters containing specific restriction enzyme sites or directly cloned into a vector of choice. In the case of prokaryotic mRNA, this procedure will not work due to the lack of poly-A tails. However, two alternatives can be utilized to circumvent this problem. One would be to add a synthetic polynucleotide RNA/DNA hybrid adapter to the end of the RNA with RNA or T4 DNA ligase. The adapter would be used to prime the 1st strand synthesis. The other would be to utilize the technique of random priming as has been done to isolate histone RNA or other mRNAs without poly-A tails. We chose the random primer method, in order to minimize the degree of difficulty involved in the procedure, and to select for smaller than full length cDNA clones for simplified sequencing.

One difficulty with the random primer method is that total RNA is made into cDNA which includes the most abundant species of RNA, rRNA and tRNA. It is not possible to remove these RNAs at the start using the oligo-dT affinity column step. However, if an organism is capable of maintaining two distinct pools of differentially expressed RNA as is Anabaena sp. strain PCC 7120, then one population of cells can be used to subtract from the other to remove transcripts common to both, which always include the rRNA and tRNA species. Anabaena sp. strain PCC 7120 produces a specialized cell, called a heterocyst, that is solely responsible for the production of ammonia from dinitrogen gas, under conditions of nitrogen deprivation. Heterocysts differentiate at regular intervals along the filaments of some cyanobacteria. In Anabaena sp. strain PCC 7120, the interval between the photosynthetic vegetative cells and flanking heterocysts is approximately ten cells. The heterocyst is surrounded by a double-layered envelope outside its cell wall. Numerous changes in the abundance of proteins accompany the differentiation of an oxygen-evolving vegetative cell into a nitrogen-fixing, anaerobic heterocyst.

Liquid hybridization of total heterocyst and vegetative cell RNA to DNA suggested that 20% of the DNA of Anabaena sp. strain PCC 7120 is expressed differentially in heterocysts (Lynn et al., 1986). Since Anabaena sp. strain PCC 7120 contains nearly 7 Mb of chromosomal and large plasmid DNA, the hybridization result means that more than 1000 genes are transcribed differentially during heterocyst development. This does not even take into account genes that are required for both cell type functions, such as the housekeeping genes. Many of these genes are also essential for both vegetative cell growth and heterocyst development. These genes are most tractable to a cDNA method, since no mutation is necessary to isolate a gene, which may not be possible for essential genes (Bauer, 1994).

5. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Construction of an Anabaena cDNA Library
5.1.1 Materials and Methods
 5.1.1.1 Materials
 All of the restriction endonucleases and the large fragment of DNA polymerase I (Klenow) used in this study were purchased from either New England BioLabs, Inc. (Beverly, Mass.), or Boehringer Mannheim Biochemicals (Indianapolis, Ind.). Deoxynucleoside triphosphates (dATP, dCTP, dTTP, and 7-deaza-dGTP), dideoxynucleoside triphosphates (ddATP, ddCTP, ddGTP, and ddTTP) were purchased from Pharmacia (Piscataway, N.J.). [$\alpha$-$^{35}$S]-dATP, [$\alpha$-$^{32}$P]-dCTP were purchased from DuPont, NEN Research Products (Boston, Mass.). Antibiotics were purchased from Sigma Chemical Co. (St. Louis, Mo.). All other chemicals were reagent grade and available commercially.

5.1.1.2 Culture Conditions

Anabaena sp. strain PCC 7120 was grown in modified Kratz and Myers medium C (K&M) or BG-11 medium (Kratz and Myers 1955; Rippka et al., 1979). In place of $Na_2HPO_4$, 1.125 mM of both $Na_2HPO_4$ and $K_2HPO_4$ were added to the K&M media. The nitrogen sources added for N+ growth were either 2.5 mM $(NH_4)_2SO_4$ (K&M+$NH_4$) or 17.6 mM $NaNO_3$ (K&M+$NO_3$). Plates contained K&M or BG-11 media with 1.3% agar (BBL purified) and 17.6 mM $NaNO_3$ if a nitrogen source was included. Cultures were grown photoautotrophically under 30–40 $\mu E/m^2/sec$ cool white fluorescent lighting at 25–30° C. in the presence of 2% $CO_2$ (large scale cultures were bubbled with a 2% $CO_2$-air mixture). Mid-log phase cells refer to cultures containing 2–6 $\mu g/ml$ of chlorophyll corresponding to $0.7 \times 10^7$ to $2.0 \times 10^7$ cells/ml.

For selective growth of *E. coli* DH5α™ antibiotics were used at concentrations of 100 $\mu g/ml$ ampicillin (Amp), 50 $\mu g/ml$ Kan and 10 $\mu g/ml$ Cml. For selective growth of Anabaena recombinants 100 $\mu g/ml$ neomycin was used for maintenance of single recombinant gene interruptions, 30 $\mu g/ml$ neomycin and spectinomycin (Spc) 20 $\mu g/ml$ and streptomycin (Str) 20 $\mu g/ml$ for plasmid borne replicating vectors.

5.1.1.3 RNA Isolation and Northern Analysis

Large scale cultures of Anabaena sp. strain PCC 7120 were synchronously induced to form heterocysts by transfer of vegetative cells from (K&M-$NH_4$) to K&M lacking a source of combined nitrogen. One liter cultures harvested at 6-hr intervals were used to prepare total RNA as described by Golden et al. (1987) with the exception that in place of vanadyl ribonucleoside complexes, aurin tricarboxylic acid was substituted for RNA destined to be used only in Northern blots. For Northern blots, approximately 20 mg samples of total RNA were denatured with glyoxal, separated by electrophoresis on a 1.0% phosphate-agarose gel and transferred to GeneScreen Plus® (DuPont) membranes with 10×SSC, in accordance with the manufacturer's protocol. The blots were hybridized with random primer labeled probes at 60° C. in 10% Dextran sulfate, 1 M NaCl, 1% sodium dodecyl sulfate (SDS) and washed at 60° C. in 2×SSC–1% SDS. Probes for Northern blots came from the cDNA inserts of two pUC19 cDNA clones, vegcDNA4 and 30hrcDNA7a, isolated with EcoRI and PstI.

5.1.1.4 Molecular Biology Techniques

Preparation, restriction enzyme digestion, and ligation of hybrid plasmid DNAs were performed by previously described techniques (Sambrook et al., 1989). Protein and DNA sequence comparisons used the GenBank databases utilizing the National Center for Biotechnology Information's (NCBI) network services and the BLAST program (Altschul et al., 1990). Multiple sequence alignments were accomplished using the ClustalV program (Higgins et al., 1992).

5.1.1.5 Construction of Stage-specific Subtracted cDNA Libraries

10 $\mu g$ of total RNA from cultures induced for 6, 12, 18, or 30 hr, or from purified heterocysts, each in 10 $\mu l$ 10 mM Tris (pH 8.0)-100 mM EDTA (pH 8.0) (TE) were heated to 70° C. for 5 min. A reaction mixture was prepared that contained 4 $\mu l$ of 10 mM each of all four dNTPs, 4.0 $\mu l$ of 5×reverse transcriptase buffer (250 $\mu l$ 1.0 M Tris pH 8.2, 250 $\mu l$ 1.0 M KCl, 30 $\mu l$ 1.0 M $MgCl_2$, 470 $\mu l$ $H_2O$), 2.0 $\mu l$ 200 mM DTT, 2 U *E. coli* DNA ligase, 2.0 $\mu l$ 0.5 mM β-AND$^+$, 1.0 $\mu l$ (=1 $\mu g$) random hexamer primers (Boehringer Mannheim Biologicals, Inc), 13 $\mu l$ $H_2O$, and 2 U RNAsin. To the mixture, the stage specific total RNA was added and mixed thoroughly. Avian Myeloblastosis Virus reverse transcriptase (50–100 U in 2–4 $\mu l$) was added and mixed thoroughly. Each reaction mixture was then incubated at 42° C. for 1.5 hr. Each mixture was then extracted with an equal volume of phenol, then of chloroform, and precipitated with 0.1 volume 7.5 M ammonium acetate and 0.6 volume of isopropanol followed by a 70% ethanol wash. The nucleic acid pellet was resuspended in 50 $\mu l$ of TE. The sample was then boiled for 1 min and quickly cooled on ice. 2.5 $\mu l$ of 10 mg/ml each of RNAse A and RNAse H were added and the mixture was incubated for 1 hour (hr) at 37° C. The RNAse was removed by adding 8 $\mu l$ of EDTA and extracting with 100 $\mu l$ of phenol. The aqueous phase was removed and the organic phase was re-extracted with 50 $\mu l$ TE to retrieve most of the single-stranded cDNA. The second aqueous phase was added to the first and the combination was chloroform-extracted and back-extracted. To each aqueous phase, 50 $\mu l$ of 7.5 M ammonium acetate and 500 $\mu l$ 100% ethanol was added, the tubes were put on dry ice for 15 min, and then centrifuged for 10 min at 4° C. to pellet the single-stranded cDNA. The pellet was washed with 70% ethanol. After re-suspension of the single stranded cDNA in 50 $\mu l$ TE, the phenol and chloroform extractions were repeated to assure complete removal of the ribonucleases.

The actual subtraction was then performed by resuspending the single-stranded cDNA in 30 $\mu l$ hybridization buffer [40 mM PIPES (pH 6.4), 1.0 mM EDTA (pH 8.0), 0.4 M NaCl, 80% formamide] (Sambrook et al., 1989). 100 $\mu g$ of vegetative cell RNA in 4–10 $\mu l$ hybridization buffer was added, mixed thoroughly and heated to 85° C. for 10 min. The hybridization mix was then allowed to cool to 37° C. and was maintained at 37° C. overnight. RNA/DNA hybrids and single-stranded cDNA were precipitated with ammonium acetate and ethanol and collected by centrifugation. The nucleic acids were resuspended in 45 $\mu l$ $H_2O$, then 6 $\mu l$ 10×low salt restriction enzyme mix and 5 U RNAGuard™ (Pharmacia) in 5 $\mu l$ were added. Three $\mu g$ of random primers and 5 $\mu l$ of 10 mM dNTPs were added and mixed. 10 U Klenow DNA Polymerase (Pharmacia) was added and the polymerization reaction run for 30 min at 37° C. Then 10 U *E. coli* DNA ligase and 2 $\mu l$ 0.5 mM AND$^+$ were added and incubation at 37° C. was continued for another hr. Proteins were removed by a phenol/chloroform extraction (1:1) and nucleic acids were precipitated with ammonium acetate and isopropanol. Following centrifugation, the nucleic acids were resuspended in 45 $\mu l$ of $H_2O$ and 5 $\mu l$ 10×T4 DNA polymerase buffer. 1 U of T4 DNA polymerase in 1.0 $\mu l$ and 1.0 $\mu l$ 10 mM dNTPs were added and the mixture was incubated for 1 hr at 37° C. 5.0 $\mu l$ of a 10 mg/ml RNAse A stock was added and incubated for another 0.5 hr at 37° C. Proteins were removed by phenol/chloroform (1:1) extraction and DNA was precipitated with ammonium acetate and 2 volumes ethanol. The blunt-ended, double-stranded cDNA was then resuspended in ligation buffer and ligated into the HincII site of pUC 19.

5.1.1.6 Documentation of Stage-specific Subtracted cDNA Library Construction 10 $\mu g$ of induced 30 hr stage total RNA was used to make 1st strand single-stranded cDNA including 5 $\mu l$ of [$\alpha^{32}$P]-dCTP (50 $\mu$Ci) without adding *E. coli* DNA ligase for one hr. After this, 5 $\mu l$ were removed and frozen. *E. coli* DNA ligase was then added for an additional 30 min and another 5 $\mu l$ sample was taken and frozen. To document the second strand synthesis, 100 $\mu g$ of induced 30 hr stage total RNA was used to make the 1st strand single-stranded cDNA and 1 mg of vegetative cell RNA was used in the subtraction. All reagents were also scaled up 10 times. Second strand synthesis included adding 5 µl of [α³²P]-dCTP (50 µCi) to the reaction and samples were taken without and with E. coli DNA ligase identical to the first strand synthesis except that half of the reaction was used in each sample. RNase was added to the samples which were incubated at 37° C. for 2 hr. Phenol/chloroform (1:1) extraction was performed and the samples were precipitated with ammonium acetate and ethanol. Samples were resuspended in 10 µl and run on a 0.7% Tris-Borate-EDTA agarose gel. The contents of the gel was transferred to GeneScreen Plus™ by capillary transfer and was subjected to autoradiography.

5.1.2 Discussion

The isolation of bacterial cDNA requires a method to create a cDNA copy of RNA without the benefit of a poly-A tail to act as a primer attachment site. To circumvent this problem, random hexamer primers were used to make both the first and 2nd cDNA strands. Since total RNA was used from each stage of differentiation, a subtraction step with vegetative cell RNA was included to remove cDNAs that came from rRNAs, tRNAs and other housekeeping RNAs. A reverse subtraction was also tried with heterocyst RNA subtracting vegetative RNA, but the efficiency of this was not as good since most heterocyst RNA preps are at least partially degraded. Gels run with radiolabeled samples of each of the stages in cDNA production indicate that cDNA is made by the reverse transcriptase step with the random primers and elongated by ligation of the shorter fragments of cDNA on the RNA template with E. coli DNA ligase. Second strand radiolabeled signal is dramatically reduced after subtraction and it seems that E. coli DNA ligase did not markedly increase cDNA size at this juncture. The procedure is uncomplicated and does not require multiple rounds of subtraction to remove unwanted cDNAs. Second strand synthesis occurs from first strand cDNAs that are not hybridized in the subtraction mixture without removal of the RNA/DNA duplexes. Cloning of the resulting double-stranded cDNAs into pUC19 acts as the purification step in this case.

5.2 Example 2

Identification of a Genomic Clone Containing sucA 5.2.1 Identification of a Bacterial Genomic Fragment With Similarity to Eukaryotic Sucrose Synthases VegCDNA4, a bacterial cDNA of approximately 200 nucleotides, was identified as a random clone that was vegetative-cell specific. This sequence showed similarity to eukaryotic sucrose synthases. Based on this finding, the inventors were motivated to examine the DNA sequence and to identify a complete DNA sequence in this region. The 200-bp cDNA was sequenced and homology searches were performed using BLAST (GenBank) algorithm computer program analyses. The results of the computer analyses indicated that the nucleic acid sequence of this cDNA encoded a portion of a protein with similarity to eukaryotic sucrose synthases and sucrose phosphate synthase.

VegCDNA4 was used as a probe against a 2000 member cosmid bank, however positively-hybridizating clones were not identified under the particular hybridization conditions initially employed. Next, vegcDNA4 was subjected to a single recombination experiment as described above. The null mutant was tested for growth on K&M medium and a 100 ml culture of the mutant was grown on BG-11+NO₃. Cells were harvested and washed with 1.0 M NaCl. The pellet was resuspended in TE and lysozyme was added and incubated for 30 min. A mixture of 10% Sarkosyl and 100 µg/ml of protease K was added and incubated for 1 hr at 37° C. The mixture was extracted with phenol, phenol-chloroform-isoamyl alcohol (PCI) and chloroform and precipitated with 60% isopropanol. The chromosomal DNA was spooled, dried and resuspended in TE.

5.2.2 Results

When used as a probe to the 2000 member Anabaena sp. strain PCC 7120 cosmid bank, no cosmids in this bank were obtained containing sucA complementary sequences. A null mutant was made by insertional inactivation in which the single recombination of the cDNA fragment contained in vegcDNA4 was fused to a non-replicating neomycin shuttle vector, pCCB111aa, and recombined into the chromosome. The mutant grew normally on plates with fixed nitrogen, but was unable to grow on plates lacking nitrogen. The heterocysts formed in the dying cultures were ultrastructurally normal at the level of light microscopy.

A Northern time-course blot of sucrose synthase indicates that the gene is not induced by nitrogen deprivation, but is constitutive in expression. The probe detects a transcript of 3.2-kb which is sufficient to contain the complete gene provided it is similar in size to the plant sucrose synthases.

5.2.3 Discussion

The sucrose synthase gene was located using a cDNA located in the vegetative cDNA bank. It was used to create a null mutant in the chromosomal copy of the gene by single recombination inactivation. The resulting mutant was Fix⁻ and could not grow on a nitrogen free medium, but maintained morphologically normal heterocysts. The Northern gel probed with the sucrose synthase gene indicates a constitutive transcript of 4.5-kb, which does not increase in quantity during differentiation. Sucrose may be the carbohydrate transferred from vegetative cells to heterocysts to fuel nitrogen fixation and anabolic requirements. The fact that the transcript was located in the vegetative cDNA library suggests that the transcript might only be found in vegetative cells, although it is possible that it might be in both.

5.3 Example 3

Cloning and DNA Sequence of Anabaena sucA

The following example describes the cloning and DNA sequence analysis of the Anabaena sucA gene, which was shown to have only 44% identity to the known plant sucrose synthase genes.

5.3.1 Materials and Methods 5.3.1.1 Isolation of a Full-length Genomic sucA Gene The mutant chromosomal DNA was then restricted with ClaI and a small sample was removed, diluted and re-ligated intra-molecularly. The ligation mix was transformed into E. coli, and Kan- and Amp-resistant colonies were isolated. pCCB111aa was excised from this clone, pCCB1015a1, by restriction digestion with BamHI to form pCCB1015am. pACYC184 was inserted into the single ClaI site of pCCB1015am and following ligation, clones were selected on 10 µg/ml chloramphenicol (Cml) and 100 µg/ml Amp to form pCCB1015an. pCCB1015an was transformed into a recA⁺ strain of E. coli MC1061, and growth was allowed to continue overnight. Plasmids were isolated from these cultures and cut with PstI, which cuts in the cDNA-pUC19 clone, but not in pACYC184. After transformation with the digest, colonies were screened for loss of the cDNA clone portion of the double vector by checking for Amp sensitivity. One resulting clone, pCCB1015ao, was cut with ClaI, and a pUC19 vector cut with AccI was ligated to the gel purified insert of the previous vector, pCCB 1015ao, to form pCCB1015ap, which contains an intact copy of the sucrose synthase gene.

5.3.1.2 Generation of Deletion Derivatives and Sequence of the sucA Gene pCCB1015ap was used to generate deletions for sequencing using random DNAse digestion in the presence of $Mn^{++}$ as described (Sambrook et al., 1989). Plasmid DNA was treated with 30 ng/ml of DNAse for 15 min in the presence of 2 mM $MnCl_2$, and linearized DNA isolated from an agarose gel. Half of the linear DNA was digested with PstI, separated on an agarose gel, 1-kb size fractions isolated from the gel which were then self-ligated and used to transform *E. coli* MC1061. Similarly, deletions in the other direction were generated using the other half of the linear DNA digested with BamHI.

DNA sequencing was performed on double-stranded templates using dideoxy chain termination sequencing with Sequenase (United States Biochemicals). Sets of deletion plasmids were sequenced from the deleted ends and some specific primers were used to fill single-stranded gaps. The 2700-nucleotide DNA segment comprising the Anabaena sucA gene is given in SEQ ID NO:1. The 806-amino acid translation of the sucA gene encoding the Anabaena sucrose synthase protein is given in SEQ ID NO:2.

5.3.2 Results

The inventors obtained and sequenced the full-length subclone containing what was determined to be the Anabaena sucA gene. This was done by taking total genomic DNA of the single recombinant mutant above, digesting with ClaI, ligating and transforming *E. coli*, selecting for $Kan^R$. The cDNA fragment was recombined out of the plasmid in vivo, and the complete sequence of the intact sucA gene was determined. This sequence is shown in FIG. 1A, FIG. 1B, FIG. 1C, FIG. 1D, and FIG. 1E. The corresponding deduced amino acid sequence is shown in FIG. 2. A comparison of the deduced amino acid sequence to that of the sucrose synthase peptide from *Arabidopsis thaliana* is shown in FIG. 2. The proteins show an overall identity of only 44%. A region near the N-terminus of the maize peptide has been shown to be phosphorylated, but this region not conserved in the Anabaena sequence. Thus the amino acid sequence of the bacterial enzyme was distinct from any eukaryotic sequence known in the prior art.

5.4 Example 4

Construction of a sucA Interposon Mutant in Anabaena

The present example describes the construction of an Anabaena strain with a mutated sucA gene, and the analysis of the corresponding phenotype. A stable double-recombinant mutant has been constructed which has a $Fix^-$ phenotype.

5.4.1 Materials and Methods

A 2-kb PCR™ fragment of the Anabaena sucA gene was generated using the following primers that incorporate an SpeI site:
5'-GGACTAGTCCATATCTCAACCGTTATCTCT-3' (SEQ ID NO:3) and
5'-GGACTAGTCCTAGGCACTAATGACTATTGA-3' (SEQ ID NO:4). The PCR™ product was cloned into the HincII site of a modified pUC19 in which the EcoRI site was removed by end-filling. A spectinomycin/streptomycin cassette (Ω cassette) (Liang et al., 1992) cut with EcoRI was cloned into the single EcoRI site in the sucA fragment. The sucA fragment carrying the Ω cassette was excised with SpeI and cloned into SpeI-digested pRL271 (Cai and Wolk, 1990).

This construct was transferred into Anabaena via conjugation and Str/Spc-resistant colonies were selected. A single colony was isolated and grown in 5 ml of liquid BG-11 until mid-log phase. Double recombinant mutants were selected by plating these cells on a BG-11 agar plate containing 2 μg/ml of streptomycin and spectinomycin, and 5% sucrose. Two colonies were selected and their genotype verified using Southern hybridization. The phenotype of the colonies was identified as $Fix^-$ by lack of growth on nitrogen-free plates.

5.4.2 Results

The phenotypes of the two sucA double-recombinants were $Fix^-$ (unable to fix nitrogen) and $Het^+$ (heterocysts present). These mutants form morphologically normal heterocysts that are defective in nitrogen fixation. Southern hybridization of the genomic DNA of the mutants and wild-type Anabaena using the sucA gene as probe demonstrated that the mutants carried an insertion the size of the interposon cassette in the sucA gene.

5.4.3 Discussion

The $Nif^-$ ($Fix^-$) phenotype of the sucA interposon mutants indicates that sucrose synthase is required for nitrogen fixation in Anabaena. It is likely that the gene product is required for the synthesis or breakdown of sucrose which is used to fuel nitrogen fixation in the heterocysts. One scenario is that sucrose synthase generates sucrose in the vegetative cells from which it is transported along the filament to the heterocysts. An alternative possibility is that sucrose is generated in the vegetative cells via sucrose phosphate synthase, transported to the heterocysts, and broken down by sucrose synthase.

5.5 Example 5

Cloning of the sucA Gene in a His-Tag System

The present example describes the cloning of the sucA gene into a his-tag system for expression in *E. coli* to demonstrate the kinetics of the bacterial enzyme. Expression in such a system involves the cloning of the sucA gene into a vector that adds a stretch of 6 histidines to the amino terminus to the peptide, expression of the fusion peptide by induction with IPTG, and one step purification from a crude extract by binding to a Ni-NTA matrix.

5.5.1 Materials and Methods

A PCR™ fragment of the coding region of the Anabaena sucA gene was generated using the plasmid carrying the sucA gene as template and the following primers:
5'-GGCGCCCATATGTGTATGCTGAATACTGCTCT-3' (SEQ ID NO:5) and
5'-CGGGATCCTTACCGATATTTATGCTGTT-3' (SEQ ID NO:6). The PCR™ fragment thus generated was cloned into pCR1000 (Invitrogen) using the A/T tail method and a clone was verified by sequencing using vector and sucA internal primers. The sucA gene was subcloned from this plasmid by digestion with NheI and BamHI, ligation into NheI/BamHI-digested pProEX-1 (GIBCO/BRL), and transformation into *E. coli* DH5α™. Induction of the his-tag SucA protein may be accomplished by growth of the strain in rich medium at 37° C. until an OD(600) of 0.4 is reached, at which time IPTG is added to 1 mM and the culture is grown at 30° C. overnight. The cells are then washed and harvested, lysed by sonication and the crude extract added to Ni-NTA resin (Qiagen) and allowed to bind. The resin may then be washed and the bound protein eluted and assayed by SDS-PAGE for yield and purity.

5.5.2 Results and Discussion

It is contemplated that expression of the sucA gene product using a his-tag system will afford rapid and quantitative purification of functional cyanobacterial sucrose synthase that can be used for kinetic characterization of the enzyme in vitro, as well as provide sufficient protein for the elicitation of antibodies. Should there be possible impairment of the SucA protein by the his-tag leader, the majority of the leader peptide can be cleaved using a specific protease that recognizes a site located immediately upstream of the SucA region (designed into the pProEX-1 vector). Por the elicitation of antibodies further purification of the SucA protein can be afforded by SDS-PAGE followed by elution.

5.6 Example 6

Preparation of Anti-SucA Antibodies

Another aspect of the present invention is the preparation of antibodies reactive against bacterial sucrose synthase for use in immunoprecipitation, affinity chromatography, and immunoelectron microscopy. The antisera may be prepared in rabbits, using methods that are well-known to those of skill in the art (see e.g., Schneider and Haselkorn, 1988).

5.6.1 Materials and Methods

Briefly, the procedure encompasses the following aspects. Gel-purified bacterial sucrose synthase protein is electroeluted, dialyzed, mixed with complete Freund's adjuvant and injected in the footpad at several locations. Subsequent boosters are given with incomplete adjuvant and finally with protein alone. Antibodies are partially purified by precipitating lipoproteins from the serum with 0.25% sodium dextran sulfate and 80 mM $CaCl_2$. Immunoglobulins are precipitated with 50% saturating ammonium sulfate, suspended in phosphate-buffered saline at 50 mg/ml and stored frozen. The antisera prepared as described may be used in Western blots of protein extracts from wheat, pea, soybean, canola and sunflower chloroplasts as well as total protein from bacterial and cyanobacterial species.

5.6.2 Results and Discussion

The inventors contemplate that the antibodies to the Anabaena SucA protein will allow one to quantitatively measure the protein concentration in cell extracts using Western blots, and allow SucA protein purification via immunoprecipitation. In addition, it can be used as a specific reagent to determine the presence of similar proteins in the cell extracts of other bacteria, and can be used to determine the presence of posttranslational modifications to the SucA protein, such as phosphorylation. Specific antibodies to the SucA protein can also be used to localize sucrose synthase in vivo through the use of in situ labeling, which will be useful for determining the mode of action for the enzyme in Anabaena.

5.7 Example 7

Methods for the Preparation of Recombinant SucA Protein

The present example describes methods for the recombinant expression of SucA protein in *E. coli* hosts. The entire sucrose synthase DNA and its fragments may be used to prepare large amounts of the corresponding proteins in *E. coli*. This is most readily accomplished using the T7 expression system. As designed by Studier, this expression system consists of an *E. coli* strain carrying the gene for T7 lysozyme and for T7 RNA polymerase, the latter controlled by a lac inducible promoter. The expression vector with which this strain can be transformed contains a promoter recognized by T7 RNA polymerase, followed by a multiple cloning site into which the desired gene can be inserted (Ashton et al., 1994).

Prior to induction, the strain grows well, because the few molecules of RNA polymerase made by basal transcription from the lac promoter are complexed with T7 lysozyme. When the inducer IPTG is added, the polymerase is made in excess and the plasmid-borne gene of interest is transcribed abundantly from the late T7 promoter. This system easily makes 20% of the cell protein the product of the desired gene. A benefit of this system is that the desired protein is often sequestered in inclusion bodies that are impossible to dissolve after the cells are lysed. This is an advantage in the present invention, because biological activity of these polypeptides is not required for purposes of raising antisera. Moreover, other expression systems are also available (Ausubel et al., 1989).

An alternate source of purified protein is anticipated to be available from the his-tag expression system described supra in Example 5.5. In this case, the fusion protein will have the his-tag leader peptide cleaved off using the rTEV protease (Gibco-BRL) and the SucA protein is then released. Purification of the SucA peptide from the his-tag and rTEV protease can be done using the Ni-NTA resin to bind the his-tag and the rTEV protease (which contains a poly-his leader) simultaneously, leaving the SucA peptide in the unbound fraction. Alternatively, the cleaved SucA peptide can be gel purified and eluted.

5.8 Example 8

Methods of Detecting and Identifying a sucA Gene In Vitro

The present example describes methods and components for kits used in the detection of suca gene(s) in other bacterial species.

5.8.1 Materials and Methods

The entire coding region of the sucA gene from Anabaena or partial fragments of the same can be used as probes in Southern hybridizations, essentially as described supra in section 4.3. Partial or complete fragments of the sucA gene can be generated by restriction digestion followed by gel purification, or by PCR™ amplification using primers based on the sequence of the sucA gene, and template either total Anabaena chromosomal DNA or plasmids containing part or all of the sucA gene. These fragments can be used as probes by labeling them with radioactive or enzymatic ligands, such as avidin/biotin.

Total DNA of the bacterial or cyanobacterial strain(s) of interest can be prepared, digested with restriction enzymes, separated on an agarose gel, and transferred to a hybridizing membrane, typically consisting of neutral or charged nylon, such as GeneScreen® or GeneScreen Plus® (DuPont). Following transfer of the DNA to the membrane and fixation of it via drying or UV irradiation, it can be probed using the labeled sucA gene fragments. Hybridization conditions would be varied using temperatures from about 40° C. to about 70° C. and salt concentrations from about 0.8 to about 1.0 M NaCl. Following hybridization the membrane would be washed free of unbound labeled DNA, and the specific hybridization detected by film, phosphorimager, or calorimetrically, depending on the label employed.

An alternative method can be employed using PCR™ to detect the presence of conserved sucA sequences in other bacterial species. Partially degenerate PCR™ primers would be synthesized based on highly conserved regions between the Anabaena sucA gene product and the known sucrose synthase sequences from plants such as Arabidopsis, maize, rice and others. PCR™ reactions would be performed using these primers, and any bands of the expected size range would be cloned, such as into a T/A cloning vector, and the sequences determined. If the sequence shows sufficiently high similarity to the known sucrose synthase genes, it will have produced a positive result.

5.8.2 Results and Discussion

It is envisioned that the use of specific DNA probes or PCR™ reactions will result in the identification of other sucrose synthase genes in other cyanobacterial and bacterial species. It is likely that these genes will have similar roles to that of sucA in Anabaena, especially in other cyanobacteria. It is envisioned that the detection of these related genes will lead to their isolation and characterization. One or more of these genes may have similar or improved utility for the transformation of plants and expression therein.

5.9 Example 9

Chimeric SucA Proteins

The present example describes the preparation of recombinant SucA proteins comprising bacterial and eukaryotic domains of the sucA genes.

5.9.1 Methods and Materials

The construction of chimeric sucrose synthase genes entails the use of gene fragments corresponding to domains or subdomains of the protein that are fused together. Fusions can be done by a variety of means, including ligation at existing compatible restriction sites, ligation at new engineered sites, or through the use of specific PCR™ reactions. These PCR™ reactions would utilize bridging primers that overlap with each other and allow initial amplification of two or more DNA fragments with engineered overlapping ends that automatically fuse after the first several rounds. By using limiting amounts of the bridging primers, it is possible to primarily generate the expected fused product (Sambrook et al., 1989).

5.9.2 Results and Discussion

It is anticipated that the construction of chimeric sucrose synthase genes will be useful for several reasons. One is for modulating the activity of the SucA protein, by means of the inclusion of functional control mechanisms such as phosphorylation, and the manipulation of the stability and degradation rate of the protein. Both of these mechanisms may be useful for engineering optimal expression of sucrose synthase in a variety of plants. Another utility for generating chimeric genes is the targeting of the protein to specific plant cell tissues or compartments, for reasons of increasing the production or yield of certain plant products. As an example of naturally occurring compartmentalization, specific sucrose synthase genes have been identified that are active primarily in root nodules or are cell wall associated (Amor et al., 1995; Kuster et al., 1993; Martinez de Ilarduya et al., 1993; Perlick and Puhler, 1993). Another use for chimeric sucrose synthases would be improvement of the enzymatic activity of the gene, either by increasing the catalytic rate, or by changing the substrate specificity or by reducing feedback inhibition.

5.10 Example 10

Methods for Introduction of the Bacterial sucA Gene Into Plant Cells

The present example describes methods useful in the introduction of the bacterial sucA gene into a plant cell, and the resulting transgenic plants derived therefrom.

5.10.1 Methods and Materials

The bacterial sucA gene may be introduced into plants by a variety of mechanisms. One of the more popular is the use of Agrobacterium binary vectors. In this protocol, the sucA gene may be engineered with specific plant promoter and processing sequences and cloned into a binary vector, such as pPZP100 (Svab et al., 1995). The vector may then be transferred to a suitable Agrobacterium strain, such as LBA4404, by electroporation, freeze-thaw or conjugation. The resultant strain of Agrobacterium is then used to infect specific plant tissues, such as leaf disks and protoplasts, by coincubation. Transformed plant tissue is identified typically by growth on selective media containing antibiotics such as Kan and gentamycin, or by the monitoring of a histochemical stain.

An alternate plant transformation protocol utilizes the biolistic mechanism, whereby tungsten beads are coated with DNA and used to bombard plant tissue. In this protocol, the sucA gene may be engineered with specific plant promoter and processing sequences and cloned into a vector containing either a chimeric uidA gene encoding β-glucuronidase or a chimeric kan gene encoding neomycin phosphotransferase, such as pFF19G or pFF19K (Maliga, 1995). This DNA is grown in *E. coli* and used to coat tungsten particles. The particles are loaded into a biolistic gun, such as the PDS-1000/He (DuPont) and used to bombard plant tissues, such as embryos, protoplasts or leaves. The plant tissue may then be cultured on selective media and the resultant plant shoots regenerated on appropriate media.

It is contemplated that other plant transformation systems such as electroporation, polyethylene glycol treatment, microinjection, liposome and virus carriers may be also used to transfer bacterial sucA gene sequences into plants. Techniques for performing these transformations are readily available (Maliga et al., 1995).

5.11 Example 11

Methods for Modulating Sucrose Synthase Activity in Plants

The present example describes methods for modulating sucrose synthase activity in transgenic plants comprising the sucA gene of the present invention.

5.11.1 Methods and Materials

Useful constructions for increasing the expression of sucrose synthase in plant tissues may include those containing fusions of constitutive or regulated promoters to the native or chimeric or mutated variants of the sucA gene from Anabaena or other bacteria. These fusions would be generated in vitro by ligating specific DNA molecules containing all or parts of specific plant promoters to the sucA gene, and using the constructs to transform plant cells as described supra in section 5.10. Useful constructions would include promoters that increase the expression of sucrose synthase in all or specific plant tissues, especially those that include storage organs, such as tubers and bulbs, or reproductive organs, such as seeds and fruits. Other constructions might include promoters that respond to specific signals, or include the addition of promoter elements that confer signal-specific or tissue-specific enhancement of expression of sucrose synthase.

5.11.2 Results and Discussion

The inventors contemplate that one of the most important uses of cyanobacterial sucrose synthase is its enhanced expression in plant cells. Since sucrose synthase has been identified as an important determinant for the sink strength of a plant tissue, increasing expression of the enzyme may allow the enhancement of fixed carbon allocation to targeted tissues. Since the cyanobacterial enzyme is unlikely to be posttranslationally regulated by phosphorylation as the plant enzymes are, it may be useful in increasing total enzyme activity in the plant cell. Improvements in carbon allocation to storage organs such as potato tubers and sugar beet roots, or to fruits or seeds, may substantially increase yields or improve quality of these tissues, by improving such characteristics as starch or sugar content. Specific enhancement of expression of the cyanobacterial gene in specific plant cells via tissue-specific promoters or promoters responsive to signals, such as ABA, gibberillin, salicylate or ethylene, is likely to provide the most benefit.

5.12 Example 12

Methods for Altering Starch and Sucrose Content in Transgenic Plants

The present example describes methods and compositions for altering starch and/or sucrose composition in transgenic plants using the sucA gene compositions of the present invention.

5.12.1 Methods and Materials

The inventors contemplate that transformation of plants with the Anabaena sucA gene appropriately expressed via tissue-specific promoters is useful in the preparation of cultivars with improved features such as enhanced starch production in potato tubers and seed grains. The Anabaena sucA gene may be fused to specific promoters or promoter elements that will allow expression of sucrose synthase in a whole plant, tissue-specific, or subcellular compartment-specific manner. Many useful promoters and promoter elements are known that are suitable. One such promoter would be the patatin promoter that is active mainly in potato tubers (Bevan et al., 1986). The fusion of the Anabaena sucA gene to the patatin promoter and expression in plants may permit an increase in the expression of sucrose synthase activity in the tuber, possibly resulting in an increase in net carbon flow into the tuber and increased starch synthesis.

Increases in sucrose synthase activity may also be accomplished through the integration of multiple copies of the Anabaena sucA gene into a target plant genome. Such multiple copies may be obtained normally from a biolistic or electroporation transformation, or by the addition of multiple copies of the sucA construction on a binary Agrobacterium vector. Transformed plants carrying increased copies of sucA can be identified by Southern hybridization of their genomic DNA with a sucA probe or by assay of sucrose synthase activity.

5.12.2 Results and Discussion

Since sucrose synthase has been identified as an important determinant for the sink strength of a plant tissue, increasing expression of the enzyme may allow the enhancement of fixed carbon allocation to targeted tissues. Since the cyanobacterial enzyme is unlikely to be posttranslationally regulated by phosphorylation as are the plant enzymes, it may be useful in increasing total enzyme activity in the plant cell. Improvements in carbon allocation to storage organs such as potato tubers and sugar beet roots, or to fruits or seeds, may substantially increase yields or improve quality of these tissues, by improving such characteristics as starch or sugar content. Specific enhancement of expression of the cyanobacterial gene in specific plant cells via tissue-specific promoters or promoters responsive to signals, such as ABA, gibberillin, salicylate or ethylene, is likely to provide the most benefit.

5.13 Example 13

Methods for Altering Nitrogen Fixation Activity in Transgenic Plants

The present example describes methods and compositions for altering nitrogen fixation activity in transgenic plants using the sucA gene compositions of the present invention.

5.13.1 Methods and Materials

The inventors contemplate a further utility of the present invention is the alteration of levels of nitrogen fixation in root nodules of leguminous crops such as soybeans, beans, alfalfa, fava beans and peas. It has recently been determined that high levels of sucrose synthase activity is present in root nodules of the fava bean that are fixing nitrogen in association with Rhizobium (Kuster et al., 1993). An increase in sucrose synthase activity in root nodules of plants that form symbioses with nitrogen fixing bacteria may result in an increase in the amount of nitrogen fixed by the plant nodules, and a beneficial increase in the fixed nitrogen content of the host plants. Such an increase in the sucrose synthase activity may be accomplished by the transformation of symbiotic plant species with Anabaena sucA gene compositions described supra in 5.11 and 5.12. Such compositions may contain specific plant promoters or promoter elements that impart nodule-specific expression to the Anabaena sucA gene.

5.13.2 Results and Discussion

The enhancement of nitrogen fixation in crop plants is likely to result in improved yield and higher quality food products, with likely improved protein content. By enhancing the allocation of fixed carbon to the root nodules, increases in nitrogen fixation by the root nodules may provide beneficial increases of fixed nitrogen to the rest of the plant. This additional nitrogen would likely be incorporated into important food tissues, such as seeds, fruits and tubers.

5.14 Example 14

Developmental Analysis of Sucrose Synthase Genes

Methods have been developed for analyzing the regulation of sucrose synthase gene expression on several levels. With a cDNA or genomic clone in hand, the first may be obtained by preparing total RNA from various tissues at different developmental stages e.g., from different segments of plants, then probing Northern blots to determine the steady-state level of sucrose synthase mRNA in each case. cDNA probes encoding conserved fragments of sucrose synthase may be used to measure total sucrose synthase mRNA level and gene specific probes to determine which gene is functioning in which tissue.

In parallel, the steady-state level of sucrose synthase protein (by western analysis using sucrose synthase-specific antibodies and/or using labeled streptavidin to detect biotinylated peptides) and its enzymatic activity may be measured to identify the most important stages of synthesis and reveal mechanisms involved in its regulation. One such study evaluates sucrose synthase expression in fast growing leaves (from seedlings at different age to mature plants), in the presence and in the absence of light. Another such study evaluates sucrose synthase expression in various cyanobacterial cells under different physiological conditions.

6. REFERENCES

The references listed below and all references cited herein are incorporated herein by reference to the extent that they supplement, explain, provide a background for, or teach methodology, techniques, and/or compositions employed herein.

U.S. Pat. No. 4,196,265.
U.S. Pat. No. 4,554,101.
U.S. Pat. No. 4,683,195.
U.S. Pat. No. 4,683,202.

U.S. Pat. No. 4,757,011.
U.S. Pat. No. 4,769,061.
U.S. Pat. No. 4,940,835.
U.S. Pat. No. 4,965,188.
U.S. Pat. No. 4,971,908.
U.S. Pat. No. 5,176,995.
Intl. Pat. Appl. Pub. No. WO 91/02071.
Intl. Pat Appl. Pub. No. WO 93/18168.
Intl. Pat. Appl. Pub. No. WO 94/0077.
Intl. Pat. Appl. Pub. No. WO 94/00583.
Abdullah et al., Biotechnology, 4:1087, 1986.
Altschul, S. F., W. Gish, W. Miller, E. W. Meyers, and D. J. Lipman, "Basic local alignment search tool," *J. Mol. Biol.*, 215:403–410, 1990.
Amor, Y., C. H. Haigler, S. Johnson, M. Wainscott, and D. P. Delmer. "A membrane-associated form of sucrose synthase and its potential role in synthesis of cellulose and callose in plants." *Proc. Natl. Acad. Sci. USA* 92:9353–9357, 1995.
Apte, S. K., P. Rowell, and W. D. P. Stewart, "Electron donation to ferredoxin in heterocysts of the $N_2$-fixing alga Anabaena cylindrica," *Proc. Roy. Soc.*, B200:1–25, 1978.
Arai, M., H. Mori, and H. Imaseki, "Expression of the gene for sucrose synthase during growth of mung bean seedlings," *Plant Cell Physiol.*, 33:503–506, 1992.
Ashton et al., *Plant Mol. Biol.*, 24:35–49, 1994.
Ausubel, F. M., Brent, R., Kingston, R. E., Moore, D. D., Seidman, J. G., Smith, J. A. and Struhl, K., "Current protocols in molecular biology," Greene Publishing Associates and Wiley-Interscience, New York, 1987.
Ausubel, F. M. et al., "Current Protocols in Molecular Biology," John Wiley & Sons, New York, 1989.
Bauer, C. C., Ph.D. Thesis. University of Chicago, 1994.
Bauer, C., L. Scappino, and R. Haselkom. "Growth of the cyanobacterium Anabaena on molecular nitrogen: NifJ is required when iron is limited," *Proc. Natl. Acad. Sci. USA*, 90:8812–8816, 1993.
Benbrook et al., In: *Proceedings Bio Expo 1986*, Butterworth, Stoneham, Mass., pp. 27–54, 1986.
Bevan, M., Barker, R., Goldsbrough, A., Jarvis, M., Kavanagh, T. and Iturriaga, G., "The structure and transcription start site of a major tuber protein gene," *Nucl. Acids Res.*, 14:4625, 1986.
Brahamsha, B. and R. Haselkom. 1991. Isolation and characterization of the gene encoding the principal sigma factor of the vegetative cell RNA polymerase from the cyanobacterium Anabaena sp. strain PCC 7120. *J. Bacteriol.*, 173:2442–2450, 1991.
Buikema, W. J. and R. Haselkorn. "Characterization of a gene controlling heterocyst development in the cyanobacterium Anabaena 7120," *Genes Dev.*, 5:321–330, 1991.
Bytebier et al., *Proc. Natl. Acad Sci. USA*, 84:5345, 1987.
Cai, Y. and Wolk, C. P., "Use of a conditionally lethal gene in Anabaena sp. strain PCC 7120 to select for double recombinants and to entrap insertion sequences," *J. Bacteriol.*, 172:3138–3145, 1990.
Callis et al., *Genes and Development*, 1:1183, 1987.
Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.
Capecchi, M. R., "High efficiency transformation by direct microinjection of DNA into cultured mammalian cells," *Cell* 22(2):479–488, 1980.
Cashmore et al., *Gen. Eng. of Plants*, Plenum Press, New York, 29–38, 1983.
Chau et al., *Science*, 244:174–181, 1989.
Chopra, S., J. Dal-favero, R. Dolferus, and Jacobs, M. "Sucrose synthase of Arabidopsis: Genomic cloning and sequence characterization. *Plant Mol. Biol.*, 18:131–134, 1992.
Choury, P. S., M. D. Latham, and P. E. Still, "Expression of two sucrose synthetase genes in endosperm and seedling cells of maize: evidence of tissue specific polymerization of protomers," *Mol. Gen. Genet.*, 203:251–255, 1986.
Clapp, D. W., "Somatic gene therapy into hematopoietic cells. Current status and future implications," *Clin. Perinatol.* 20(1):155–168, 1993.
Cossar, J. D., P. Rowell, and W. D. P. Stewart, "Thioredoxin as a modulator of glucose-6-phosphate dehydrogenase in a N2-fixing cyanobacterium," *J. Gen. Microbiol.*, 130:991–998, 1984.
Cristou et al., *Plant Physiol*, 87:671–674, 1988.
Curiel, D. T., Agarwal, S., Wagner, E., and Cotten, M., "Adenovirus enhancement of transferrin-polylysine-mediated gene delivery," *Proc. Natl. Acad. Sci. USA* 88(19):8850–8854, 1991.
Curiel, D. T., Wagner, E., and Cotten, M., Bimstiel, M. L., Agarwal, S., Li, C. M., Loechel, S., and Hu, P. C. high-efficiency gene transfer mediated by adenovirus coupled to DNA-polylysine complexes," *Hum. Gen. Ther.* 3(2):147–154, 1992.
Desprez, T., Amselem, J., Chiapello, H., Caboche, M. and Hofte, H, The *Arabidopsis thaliana* transcribed genome: the GDR cDNA program. GenBank Accession #Z26557.
Dhir et al., *Plant Cell Reports*, 10:97, 1991.
Duggan, J. X. and L. E. Anderson, "Light regulation of enzyme activity in Anacystis nidulans (Richt.)," *Planta*, 122:293–297, 1975.
Eglitis, M. A., and Anderson, W. F., "Retroviral vectors for introduction of genes into mammalian cells," *Biotechniques* 6(7):608–614, 1988.
Eglitis, M. A., Kantoff, P. W., Kohn, D. B., Karson, E., Moen, R. C., Lothrop, C. D., Blaese, R. M., and Anderson, W. F., "Retroviral-mediated gene transfer into hemopoietic cells," *Adv. Exp. Med Biol.* 241:19–27, 1988.
Fraley et al., *Biotechnology*, 3:629, 1985.
Fraley et al., *Proc. Natl. Acad Sci. USA*, 80:4803, 1983.
Fromm et al., *Nature*, 319:791, 1986.
Fromm, M., Taylor, L. P., and Walbot, V., "Expression of genes transferred into monocot and dicot plant cells by electroporation," *Proc. Natl. Acad. Sci. USA* 82(17): 5824–5828, 1985.
Fujimura et al., *Plant Tissue Culture Letters*, 2:74, 1985.
Fynan, E. F., Webster, R. G., Fuller, D. H., Haynes, J. R., Santoro, J. C., and Robinson, H. L., "DNA vaccines: protective immunizations by parenteral, mucosal, and gene gun inoculations," *Proc. Natl. Acad. Sci. USA* 90d(24):11478–11482, 1993.
Gefter et al., *Somatic Cell Genet*. 3:231–236, 1977.
Geigenberger, P., and M. Stitt, "Sucrose synthase catalyses a readily reversible reaction in vivo in developing potato tubers and other plant tissues," *Planta* 189:329–339, 1993.
Gleason F. K., "Activities of two dissimilar thioredoxins from the cyanobacterium Anabaena sp. strain PCC 7120," *J. Bacteriol.*, 174:2592–8, 1992.
Goding, "Monoclonal Antibodies: Principles and Practice," pp. 60–74. 2nd Edition, Academic Press, Orlando, Fla., 1986.
Golden et al., "Genetic engineering of the cyanobacterial chromosome," *Methods Enzymol.*, 153:215–231, 1987.
Goding, "Monoclonal Antibodies: Principles and Practice," *2nd Edition, Academic Press*, 1986

Graham, F. L., and van der Eb, A. J., "Transformation of rat cells by DNA of human adenovirus 5," *Virology* 54(2):536–539, 1973.

Harlow, E. and Lane, D. "Antibodies: A Laboratory Manual," Cold Spring Harbor Laboratory, Cold Spring Harbor, N.Y., 1988.

Hess, *Intern Rev. Cytol.*, 107:367, 1987.

Higgins, D. G., A. J. Bleasby, and R. Fuchs, "CLUSTAL V: improved software for multiple sequence alignment," *Computer Appl. Biosci*., 8(2): 189–91, 1992, 1992.

Horsch et al., *Science*, 227:1229–1231, 1985.

Huang, J.-W., J.-T. Chen, W.-P. Yu, L.-F. Shyur, A.-Y. Wang, H.-Y. Sung, P.-D.

Lee, and J.-C. Su, "Complete structures of three rice sucrose synthase isogenes and differential regulation of their expressions," *Biosci. Biotech. Biochem*., 60:233–239, 1996.

Huber, S. C., and J. Huber L, "Role and regulation of sucrose-phosphate synthase in higher plants," In R. L. Jones, C. R. Somerville and V. Walbot (Ed.), *Ann. Rev. of Plant Physiol. Plant Molec. Biol*., Annual Reviews, Inc., Palo Alto, Calif., p. 431–444, 1996.

Jameson and Wolf, "The Antigenic Index: A Novel Algorithm for Predicting Antigenic Determinants," *Compu. Appl. Biosci*., 4(l):181–6, 1988

Johnston, S. A., and Tang, D. C., "Gene gun transfection of animal cells and genetic immunization," *Methods Cell. Biol*. 43(A):353–365, 1994.

Jorgensen et al., *Mol. Gen. Genet*., 207:471, 1987.

Keller et al., *EMBO J*, 8:1309–14, 1989.

Klee et al., In: *Plant DNA Infectious Agents*, T. Hohn and J. Schell, eds., Springer-Verlag, New York pp. 179–203, 1985.

Klein et al., *Nature*, 327:70, 1987.

Klein et al., *Proc. Natl. Acad. Sci. USA*, 85:8502–8505, 1988.

Kohler and Milstein, *Nature*, 256:495–497, 1975.

Kohler and Milstein, *Eur. J. Immunol*. 6:511–519, 1976.

Kratz, W. A., and J. Myers. "Nutrition and growth of several blue-green algae," *Am. J Bot*., 42:282–287, 1955.

Kuby, J., "Immunology" 2nd Edition. W. H. Freeman & Company, New York, 1994.

Kuster, H., M. Fruhling, A. M. Perlick, and A. Puhler, "The sucrose synthase gene is predominantly expressed in the root nodule tissue of *Vicia faba*," *Mol. Plant Microbe Interact*., 6:507–514, 1993.

Kyte and Doolittle, *J. Mol. Biol*., 157:105–132, 1982.

Langridge et al., *Proc. Natl. Acad. Sci. USA*, 86:3219–3223, 1989.

Liang, J., Scappino, L. and Haselkorn, R., "The patA gene product, which contains a region similar to CheY of *Escherichia coli*, controls heterocyst pattern formation in the cyanobacterium Anabaena 7120," *Proc. Natl. Acad. Sci, USA*, 89:5655–5659, 1992.

Lindstrom et al., *Developmental Genetics*, 11:160, 1990.

Lorz et al., *Mol. Gen. Genet*., 199:178, 1985.

Lu, L., Xiao, M., Clapp, D. W., Li, Z. H., and Broxmeyer, H. E., "High efficiency retroviral mediated gene transduction into single isolated immature and replatable CD34(3+) hematopoietic stem/progenitor cells from human umbilical cord blood," *J. Exp. Med*. 178(6): 2089–2096, 1993.

Luo et al., *Plant Mol. Biol. Reporter*, 6:165, 1988.

Lynn, M. E., J. A. Bantle, and J. D. Ownby, "Estimation of gene expression in heterocysts of *Anabaena variabilis* by using DNA-RNA hybridization," *J. Bacteriol*., 167:940–946, 1986.

Maddock et al., *Third International Congress of Plant Molecular Biology*, Abstract 372, 1991.

Maliga, P., "Biolistic transformation of tobacco cells with nuclear drug resistance genes," In P. Maliga, D. F. Klessig, A. R. Cashmore, W. Gruissem and J. E. Varner (Eds.), *Methods in Plant Molecular Biology: a laboratory course manual*, p. 37–54, Cold Spring Harbor Press, Cold Spring Harbor, 1995.

Maliga, P., D. F. Klessig, A. R. Cashmore, W. Gruissem, and J. E. Varner, "Methods in Plant Molecular Biology: a laboratory course manual," p. 446, Cold Spring Harbor Press, Cold Spring Harbor, 1995.

Maloy, et al., "Microbial Genetics" 2nd Edition. Jones and Bartlett Publishers, Boxton, Mass., 1994.

Marcotte et al., *Nature*, 335:454, 1988.

Martinez de Ilarduya, O., J. Vicente-Carbajosa, B. S. de la Hoz, and P. Carbonero, "Sucrose synthase genes in barley: cDNA cloning of the Ss2 type and tissue-specific expression of Ss1 and Ss2," *FEBS Lett*. 320:177–181, 1993.

McCabe et al., *Biotechnology*, 6:923, 1988.

Natarajan, K. and A. Datta. "Molecular cloning and analysis of the NAGI cDNA coding for glucosamine-6-phosphate deaminase from *Candida albicans*," *J. Biol. Chem*., 268:9206–9214, 1993.

Neuhaus et al., *Theor. Appl. Genet*., 75:30, 1987.

Odell et al., *Nature*, 313:810, 1985.

Oliver, S. G., Van der Aart, and [145 others]. "The complete DNA sequence of yeast chromosome III," *Nature*, 357:38–46, 1992.

Omirulleh et al., *Plant Molecular Biology*, 21:415–428, 1993.

Pena et al., *Nature*, 325:274, 1987.

Perlick, A. M., and A. Puhler, "A survey of transcripts expressed specifically in root nodules of broadbean (*Vicia faba* L.)," *Plant Mol. Biol*., 22:957–970, 1993.

Pearson, W. R. and D. J. Lipman. "Improved tools for biological sequence comparison," *Proc. Natl. Acad. Sci. USA*, 85:2444–2448, 1988.

Plumbridge, J. and A. Kolb. "Cap and Nag Repressor Binding to the Regulatory Regions of the nagE-B and manx genes of *Escherichia coli*," *J. Mol. Biol*., 217:661–679, 1991.

Poszkowski et al., *EMBO J*., 3:2719, 1989.

Potrykus et al., *Mol. Gen. Genet*., 199:183, 1985.

Prokop, A. and Bajpai, R. K., Ann. N.Y. Acad. Sci. Vol. 646, 1991.

Rippka, R., J. Dereulles, J. B. Waterbury, M. Herdman, and R. Y. Stanier. "Generic assignments, strain histories and properties of pure cultures of cyanobacteria," *J. Gen. Microbiol*., 11:1–61, 1979.

Rogers et al., In: *Methods For Plant Molecular Biology*, A. Weissbach and H.

Weissbach, eds., Academic Press Inc., San Diego, Calif. 1988.

Rogers et al., *Meth. in Enzymol*., 153:253–277, 1987.

Salanoubat, M., and G. Belliard. "Molecular cloning and sequencing of sucrose synthase cDNA from potato (*Solanum tuberosum* L.): Preliminary characterization of sucrose synthase mRNA distribution," *Gene*, 60:47–56, 1987.

Sambrook et al., "Molecular Cloning: A Laboratory Manual," Cold Spring Harbor Laboratory, Cold Spring Harbor, N.Y., 1989.

Schilling, N., and K. Ehlnsperger, "Cellular differentiation of sucrose metabolism in *Anabaena variabilis*," *Z. Naturforsch*., 40c:776–779, 1985.

Schneider and Haselkom, "RNA polymerase subunit homology among cyanobacteria, other eubacteria and archaebacteria," *J. Bacteriol*. 170:4136–4140, 1988.

Segal, I. H., "Biochemical Calculations" 2nd Edition. John Wiley & Sons, New York, 1976.

Simpson, *Science*, 233:34, 1986.

Spielmann et al., *Mol. Gen. Genet.*, 205:34, 1986.

Sturm, A., Nucleotide sequence of a cDNA clone coding for sucrose synthase from carrot (*Daucus carota* L. cv. Nantaise) GenBank Accession #X75332.

Svab, Z., P. Hajdukiewicz, and P. Maliga, "Generation of transgenic tobacco plants by cocultivation of leaf disks with Agrobacterium pPZP binary vectors,". In P. Maliga, D. F. Klessig, A. R. Cashmore, W. Gruissem and J. E. Varner (Eds.), *Methods in Plant Molecular Biology*. p. 55–78, Cold Spring Harbor Press, Cold Spring Harbor, 1995.

Toriyama et al., *Theor Appl. Genet.*, 73:16, 1986.

Uchimiya et al., *Mol. Gen. Genet.*, 204:204, 1986.

Van Tunen et al., *EMBO J.*, 7:1257, 1988.

Vasil et al., "Herbicide-resistant fertile transgenic wheat plants obtained by microprojectile bombardment of regenerable embryogenic callus," *Biotechnology*, 10:667–674, 1992.

Vasil, *Biotechnology*, 6:397, 1988.

Vodkin et al., *Cell*, 34:1023, 1983.

Vogel et al., *J. Cell Biochem.*, (Suppl) 13D:312, 1989.

Wagner, E., Zatloukal, K., Cotten, M., Kirlappos, H., Mechtler, K., Curiel, D. T., and Birnstiel, M. L., "Coupling of adenovirus to transferrin-polylysine/DNA complexes greatly enhances receptor-mediated gene delivery and expression of transfected genes," *Proc. Natl. Acad. Sci. USA* 89(13):6099–6103, 1992.

Weissbach and Weissbach, *Methods for Plant Molecular Biology*, (Eds.), Academic Press, Inc., San Diego, Calif., 1988.

Wenzler et al., *Plant Mol. Biol.*, 12:41–50, 1989.

Werr, W., W. B. Frommer, C. Maas, and P. Starlinger. "Structure of the sucrose synthase gene on chromosome 9 of *Zea mays*," *EMBO J.*, 4:1373–1380, 1985.

Witters and Kemp, "Insulin activation of acetyl-CoA carboxylase by inhibition of the 5N-AMP-activated protein kinase," *J. Biol. Chem.*, 267:2864–2867, 1992.

Wolf et al., *Compu. Appl. Biosci.*, 4(1):187–91 1988.

Wong, T. E., and Neumann, E., "Electric field mediated gene transfer," *Biochim. Biophys. Res. Commun.* 107(2):584–587, 1982.

Yamada et al., *Plant Cell Rep.*, 4:85, 1986.

Yang et al., *Proc. Natl. Acad. Sci. USA*, 87:4144–48, 1990.

Zatloukal, L., Wagner, E., Cotten, M., Phillips, S., Plank, C., Steinlein, P., Curiel, D. T., and Birnstiel, M. L., "Transferrinfection: a highly efficient way to express gene constructs in eukaryotic cells," *Ann. N.Y. Acad Sci.*, 660:136–153, 1992.

Zhou et al., *Methods in Enzymology*, 101:433, 1983.

Zrenner, R., M. Salanoubat, L. Willmitzer, and U. Sonnewald, "Evidence of the crucial role of sucrose synthase for sink strength using transgenic potato plants (*Solanum tuberosum* L.)," *Plant J.*, 7:97–107, 1995.

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2700 base pairs
      (B) TYPE: nucleic acid
      (C) STRANDEDNESS: single
      (D) TOPOLOGY: linear (xi) SEQUENCE DESCRIPTION: SEQ ID NO:1:

```
CTACGAAAAA TATTAAGCAT CTAAACTATA ACCACAGTAT AAAAAATTGT CTATCTTTAG      60

TTAGAGCCAA TAATACCTAG TTGTCGATAT TCTAAGTAAA TAAGAACAAG GTTTGATACA     120

AAGATAAAAA CACAGATAGA TGAATTTATC TGTGTTTTTT TGCATTTGTA GGTGTTGAGA     180

TTCTAGGTTG TTAGCCTACG TTACCCTAGA AAGCAAATAG GTTCAATCTT CCTTCATTTA     240

AGGGGTGAAT ATGTCAGAAT TGATGCAAGC GATTTTAGAT AGTGAAGAAA AACATGATTT     300

GCGTGGATTT ATTAGTGAGT TGCGTCAGCA AGATAAAAAT TACCTGCTAC GCAACGATAT     360

ACTGAATGTG TATGCTGAAT ACTGCTCTAA GTGCCAGAAA CCGGAAACTT CTTATAAGTT     420

TTCTAATCTA AGTAAACTTA TTTACTACAC TCAAGAAATA ATTCAAGAAG ATTCCAATTT     480

TTGCTTCATT ATTCGTCCTA AGATTGCTGC TCAAGAGGTA TATCGACTCA CCGCAGATTT     540

AGATGTGGAG CCGATGACTG TGCAGGAATT GTTGGATCTG CGCGATCGCC TAGTTAATAA     600

ATTCCATCCT TATGAAGGCG ATATATTAGA ACTAGATTTC GGCCCCTTCT ACGATTACAC     660

CCCAACCATC CGCGATCCCA AGAATATTGG CAAGGGTGTA CAATATCTCA ACCGTTATCT     720

CTCCAGTAAA CTTTTTCAAG ACTCGCAACA ATGGCTGGAA AGTCTGTTTA ATTTCTTGCG     780
```

-continued

```
CCTACATAAT TACAATGGTA TTCAACTACT AATAAACCAT CAAATTCAAT CACAGCAACA    840

ATTATCACAG CAAGTTAAAA ACGCGCTTAA CTTTGTGAGC GATCGCCCCA ATGATGAACC    900

CTACGAACAA TTCCGGCTGC AACTACAAAC TATGGGTTTT GAGCCGGGGT GGGGTAATAC    960

AGCTTCTCGT GTGCGGGATA CCTTAAACAT TTTGGATGAA TTGATTGACT CTCCCGACCC   1020

CCAAACCCTG GAAGCTTTTA TCTCTCGCAT CCCGATGATT TTCAGAATCG TCTTAGTTTC   1080

AGCCCACGGT TGGTTCGGAC AAGAGGGGGT TTTAGGTCGT CCAGATACTG GTGGTCAAGT   1140

AGTGTACGTC CTTGACCAAG CTAAGAATTT AGAAAAGCAA CTGCAAGAAG ATGCCATACT   1200

TGCAGGTTTA GAGGTATTGA ACGTCCAGCC CAAGGTAATT ATCCTCACCC GTCTGATTCC   1260

TAATAGTGAC GGAACGCTTT GTAACCAAAG GTTAGAAAAA GTCTACGGTA CAGAGAACGC   1320

CTGGATTTTG CGTGTACCTC TGCGGGAGTT TAACCCCAAG ATGACGCAGA ACTGGATTTC   1380

TCGATTCGAG TTTTGGCCTT ATCTAGAAAC CTTTGCCATT GACTCAGAAA GAGAATTGTT   1440

GGCAGAATTC CAAGGTAGAC CAGACTTAAT CGTGGGTAAT TATACTGACG GAACTTAGT    1500

TGCTTTTCTG TTGACGCGAC GGATGAAAGT TACCCAATGC AACATCGCTC ATGCTTTAGA   1560

AAAATCCAAA TACTTGTTTA GTAACCTCTA CTGGCAAGAT TTGGAAGAAA AATATCATTT   1620

CTCTTTACAA TTCACGGCTG ATTTAATAGC TATGAATGCT GCTAACTTCG TCATCAGCAG   1680

CACCTATCAA GAAATTGTTG GCACACCAGA CAGTATAGGG CAGTATGAGT CTTACAAATG   1740

CTTTACCATG CCGGAACTGT ATCATGTGGT CAACGGCATT GAATTATTTA GCCCCAAATT   1800

TAACGTTGTA CCGCCTGGTG TGAATGAAAA TTCCTACTTT CCCTACACAC AAACTCAAAA   1860

CAGAATAGAA AGCGATCGCG ATCGCCTAGA GGAAATGCTG TTTACCCTAG AAGATTCTAG   1920

CCAAATCTTC GGCAAACTCG ACGACCCAAA TAAGCGTCCT ATTTTCTCAA TGGCGCGACT   1980

TGACCGAATT AAAAACCTCA CAGGTTTGGC AGAATGCTTT GGTCAAAGTC AAGAATTGCA   2040

AGAACGTTGC AACTTAATTT TAGTTGCAGG TAAGCTGCGT ATCGAAGAAT CAGAAGATAA   2100

CGAAGAAAAA GACGAAATCG TCAAACTTTA CCGGATTATT GACGAATACA ACCTGCATGG   2160

CAAAATTCGC TGGTTAGGTG TGCGCTTATC CAAAAATGAC TCCGGTGAAA TTTATCGCGT   2220

CATTTGCGAT CGCCAAGGCA TTTTTGTACA GCCAGCATTA TTTGAAGCCT TGGGTTGAC    2280

AATCCTGGAG TCAATGATTT CCGGATTGCC AACATTTGCT ACCCAATTTG GGGGCCATT    2340

GGAGATTATT CAGGATAAGA TTAATGGCTT CTACATTAAC CCTACTCATC TAGAAGAAAC   2400

AGCCACAAAA ATTCTTGATT TCGTCACCAA ATGCGAACAA ATCCTAACT ATTGGAACAT    2460

AATTTCCGAG AAAGCCATTG ACAGAGTATA TAGTACATAC ACCTGGAAAA TACACACAAC   2520

TAAGCTGTTA ACCTTAGCTC GGATTTACGG CTTCTGGAAT TTTACCTCGA AAGAAAAACG   2580

CGAAGATTTA TTACGCTACC TTGAGTCCCT GTTCTACTTA ATTTACAAGC CAGAGCGCA    2640

ACAACTATTA GAACAGCATA AATATCGGTA ATTTGTGATT AGTCAATAGT CATTAGTGCC   2700
```

(2) INFORMATION FOR SEQ ID NO:2:

(i) SEQUENCE CHARACTERISTICS:
        (A) LENGTH: 806 amino acids
        (B) TYPE: amino acid
        (C) STRANDEDNESS:
        (D) TOPOLOGY: linear (xi) SEQUENCE DESCRIPTION: SEQ ID NO:2:

```
Met Ser Glu Leu Met Gln Ala Ile Leu Asp Ser Glu Glu Lys His Asp
 1               5                  10                  15
```

```
Leu Arg Gly Phe Ile Ser Glu Leu Arg Gln Gln Asp Lys Asn Tyr Leu
            20                  25                  30

Leu Arg Asn Asp Ile Leu Asn Val Tyr Ala Glu Tyr Cys Ser Lys Cys
            35                  40                  45

Gln Lys Pro Glu Thr Ser Tyr Lys Phe Ser Asn Leu Ser Lys Leu Ile
 50                  55                  60

Tyr Tyr Thr Gln Glu Ile Ile Gln Glu Asp Ser Asn Phe Cys Phe Ile
 65                  70                  75                  80

Ile Arg Pro Lys Ile Ala Ala Gln Glu Val Tyr Arg Leu Thr Ala Asp
                85                  90                  95

Leu Asp Val Glu Pro Met Thr Val Gln Glu Leu Leu Asp Leu Arg Asp
            100                 105                 110

Arg Leu Val Asn Lys Phe His Pro Tyr Glu Gly Asp Ile Leu Glu Leu
            115                 120                 125

Asp Phe Gly Pro Phe Tyr Asp Tyr Thr Pro Thr Ile Arg Asp Pro Lys
            130                 135                 140

Asn Ile Gly Lys Gly Val Gln Tyr Leu Asn Arg Tyr Leu Ser Ser Lys
145                 150                 155                 160

Leu Phe Gln Asp Ser Gln Gln Trp Leu Glu Ser Leu Phe Asn Phe Leu
                165                 170                 175

Arg Leu His Asn Tyr Asn Gly Ile Gln Leu Leu Ile Asn His Gln Ile
            180                 185                 190

Gln Ser Gln Gln Gln Leu Ser Gln Gln Val Lys Asn Ala Leu Asn Phe
            195                 200                 205

Val Ser Asp Arg Pro Asn Asp Glu Pro Tyr Glu Gln Phe Arg Leu Gln
            210                 215                 220

Leu Gln Thr Met Gly Phe Glu Pro Gly Trp Gly Asn Thr Ala Ser Arg
225                 230                 235                 240

Val Arg Asp Thr Leu Asn Ile Leu Asp Glu Leu Ile Asp Ser Pro Asp
                245                 250                 255

Pro Gln Thr Leu Glu Ala Phe Ile Ser Arg Ile Pro Met Ile Phe Arg
            260                 265                 270

Ile Val Leu Val Ser Ala His Gly Trp Phe Gly Gln Glu Gly Val Leu
            275                 280                 285

Gly Arg Pro Asp Thr Gly Gly Gln Val Val Tyr Val Leu Asp Gln Ala
            290                 295                 300

Lys Asn Leu Glu Lys Gln Leu Gln Glu Asp Ala Ile Leu Ala Gly Leu
305                 310                 315                 320

Glu Val Leu Asn Val Gln Pro Lys Val Ile Leu Thr Arg Leu Ile
                325                 330                 335

Pro Asn Ser Asp Gly Thr Leu Cys Asn Gln Arg Leu Glu Lys Val Tyr
            340                 345                 350

Gly Thr Glu Asn Ala Trp Ile Leu Arg Val Pro Leu Arg Glu Phe Asn
            355                 360                 365

Pro Lys Met Thr Gln Asn Trp Ile Ser Arg Phe Glu Phe Trp Pro Tyr
370                 375                 380

Leu Glu Thr Phe Ala Ile Asp Ser Glu Arg Glu Leu Leu Ala Glu Phe
385                 390                 395                 400

Gln Gly Arg Pro Asp Leu Ile Val Gly Asn Tyr Thr Asp Gly Asn Leu
                405                 410                 415

Val Ala Phe Leu Leu Thr Arg Arg Met Lys Val Thr Gln Cys Asn Ile
            420                 425                 430
```

-continued

```
Ala His Ala Leu Glu Lys Ser Lys Tyr Leu Phe Ser Asn Leu Tyr Trp
        435                 440                 445

Gln Asp Leu Glu Glu Lys Tyr His Phe Ser Leu Gln Phe Thr Ala Asp
        450                 455                 460

Leu Ile Ala Met Asn Ala Ala Asn Phe Val Ile Ser Ser Thr Tyr Gln
465                 470                 475                 480

Glu Ile Val Gly Thr Pro Asp Ser Ile Gly Gln Tyr Glu Ser Tyr Lys
                485                 490                 495

Cys Phe Thr Met Pro Glu Leu Tyr His Val Val Asn Gly Ile Glu Leu
                500                 505                 510

Phe Ser Pro Lys Phe Asn Val Val Pro Pro Gly Val Asn Glu Asn Ser
        515                 520                 525

Tyr Phe Pro Tyr Thr Gln Thr Gln Asn Arg Ile Glu Ser Asp Arg Asp
        530                 535                 540

Arg Leu Glu Glu Met Leu Phe Thr Leu Glu Asp Ser Ser Gln Ile Phe
545                 550                 555                 560

Gly Lys Leu Asp Asp Pro Asn Lys Arg Pro Ile Phe Ser Met Ala Arg
                565                 570                 575

Leu Asp Arg Ile Lys Asn Leu Thr Gly Leu Ala Glu Cys Phe Gly Gln
                580                 585                 590

Ser Gln Glu Leu Gln Glu Arg Cys Asn Leu Ile Leu Val Ala Gly Lys
        595                 600                 605

Leu Arg Ile Glu Glu Ser Glu Asp Asn Glu Glu Lys Asp Glu Ile Val
610                 615                 620

Lys Leu Tyr Arg Ile Ile Asp Glu Tyr Asn Leu His Gly Lys Ile Arg
625                 630                 635                 640

Trp Leu Gly Val Arg Leu Ser Lys Asn Asp Ser Gly Glu Ile Tyr Arg
                645                 650                 655

Val Ile Cys Asp Arg Gln Gly Ile Phe Val Gln Pro Ala Leu Phe Glu
                660                 665                 670

Ala Phe Gly Leu Thr Ile Leu Glu Ser Met Ile Ser Gly Leu Pro Thr
                675                 680                 685

Phe Ala Thr Gln Phe Gly Gly Pro Leu Glu Ile Ile Gln Asp Lys Ile
        690                 695                 700

Asn Gly Phe Tyr Ile Asn Pro Thr His Leu Glu Glu Thr Ala Thr Lys
705                 710                 715                 720

Ile Leu Asp Phe Val Thr Lys Cys Glu Gln Asn Pro Asn Tyr Trp Asn
                725                 730                 735

Ile Ile Ser Glu Lys Ala Ile Asp Arg Val Tyr Ser Thr Tyr Thr Trp
                740                 745                 750

Lys Ile His Thr Thr Lys Leu Leu Thr Leu Ala Arg Ile Tyr Gly Phe
        755                 760                 765

Trp Asn Phe Thr Ser Lys Glu Lys Arg Glu Asp Leu Leu Arg Tyr Leu
        770                 775                 780

Glu Ser Leu Phe Tyr Leu Ile Tyr Lys Pro Arg Ala Gln Gln Leu Leu
785                 790                 795                 800

Glu Gln His Lys Tyr Arg
                805
```

(2) INFORMATION FOR SEQ ID NO:3:

(i) SEQUENCE CHARACTERISTICS:
        (A) LENGTH: 29 base pairs
        (B) TYPE: nucleic acid -continued

```
            (C) STRANDEDNESS: single
            (D) TOPOLOGY: linear (xi) SEQUENCE DESCRIPTION: SEQ ID NO:3:

GGACTAGTCC ATATCTCAAC CGTTATCTC                                    29

(2) INFORMATION FOR SEQ ID NO:4:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:4:

GGACTAGTCC TAGGCACTAA TGACTATTGA                                   30

(2) INFORMATION FOR SEQ ID NO:5:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (xi) SEQUENCE DESCRIPTION: SEQ ID NO:5:

GGCGCCCATA TGTGTATGCT GAATACTGCT CT                                32

(2) INFORMATION FOR SEQ ID NO:6:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (xi) SEQUENCE DESCRIPTION: SEQ ID NO:6:

CGGGATCCTT ACCGATATTT ATGCTGTT                                     28
```

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A polynucleotide comprising a gene encoding a sucrose synthase polypeptide that comprises the amino acid sequence of SEQ ID NO: 2, said gene operably linked to a heterologous promoter that expresses said gene.

2. The polynucleotide of claim 1, wherein said heterologous promoter is a plant expressible promoter.

3. The polynucleotide of claim 2, wherein said heterologous promoter is selected from the group consisting of a lectin, glnA, CaMV35S, lac inducible, corn sucrose synthetase 1, corn alcohol dehydrogenase 1, corn light harvesting complex, corn heat shock protein, pea small subunit RuBP carboxylase, mannopine synthase, nopaline synthase, petunia chalcone isomerase, bean glycine rich protein 1, potato patatin, and an S-E9 small subunit RuBP carboxylase promoter.

4. The polynucleotide of claim 1, wherein said heterologous promoter is a bacterial expressible promoter.

5. The polynucleotide of claim 4, wherein said heterologous promoter is selected from the group consisting of a tac, trp, lac, T7, glynA and a sucA promoter.

6. The polynucleotide of claim 1, wherein said gene comprises the sequence of SEQ ID NO: 1.

7. The polynucleotide of claim 1, wherein said gene encodes an Anabaena sucrose synthase polypeptide.

8. The polynucleotide of claim 1, comprised within an expression vector.

9. The polynucleotide of claim 8, comprised within a plasmid or a viral vector.

10. The polynucleotide of claim 1, comprised within a host cell.

11. The polynucleotide of claim 10, comprised within a prokaryotic host cell.

12. The polynucleotide of claim 11, comprised within a bacterial or cyanobacterial host cell.

13. The polynucleotide of claim 12, comprised within an E. coli or Agrobacterium sp. host cell.

14. The polynucleotide of claim 13, comprised within an *Agrobacterium tumefaciens* host cell.

15. The polynucleotide of claim 10, comprised within an eukaryotic host cell.

16. The polynucleotide of claim 15, comprised within an animal, yeast or plant host cell.

17. The polynucleotide of claim 16, comprised within a monocotyledonous plant host cell.

18. The polynucleotide of claim 17, comprised within a maize, rice, wheat, barley, oats, rye, asparagus, or a grain or cereal plant host cell.

19. The polynucleotide of claim 15, comprised within a dicotyledonous plant host cell.

20. The polynucleotide of claim 19, comprised within a sugar beet, soybean, alfalfa, fava bean, pea, bean, tomato, potato, tobacco, apple, cherry, pear, strawberry, raspberry, legume, tuber, or fruit plant host cell.

21. The polynucleotide of claim 19, wherein said dicotyledenous plant is a potato plant.

22. A vector comprising a gene encoding a sucrose synthase polypeptide that comprises the amino acid sequence of SEQ ID NO: 2, said gene operably linked to a heterologous promoter that expresses said gene.

23. The vector of claim 22, further defined as a plasmid or a viral vector.

24. The vector of claim 22, wherein said gene comprises the sequence of SEQ ID NO: 1.

25. The vector of claim 22, comprised within a host cell.

26. The vector of claim 25, comprised within a prokaryotic host cell.

27. The vector of claim 26, comprised within a bacterial or cyanobacterial host cell.

28. The vector of claim 27, comprised within an *E. coli* or Agrobacterium sp. host cell.

29. The vector of claim 28, comprised within an *Agrobacterium tumefaciens* host cell.

30. The vector of claim 25, comprised within a eukaryotic host cell.

31. The vector of claim 30 comprised within a plant host cell.

32. The vector of claim 31 comprised within a monocotyledonous or dicotyledonous plant host cell.

33. The vector of claim 32 comprised within a maize, rice, wheat, barley, oats, rye, asparagus, grain, cereal, sugar beet, soybean, alfalfa, fava bean, pea, bean, tomato, potato, tobacco, apple, cherry, pear, strawberry, raspberry, legume, tuber, or fruit plant host cell.

34. A host cell comprising a gene encoding a sucrose synthase polypeptide that comprises the amino acid sequence of SEQ ID NO: 2, said gene operably linked to a heterologous promoter that expresses said gene.

35. The host cell of claim 34 wherein said heterologous promoter is a plant-expressible promoter.

36. The host cell of claim 35 wherein said heterologous promoter is a lectin, glnA, CaMV35S, lac inducible, corn sucrose synthetase 1, corn alcohol dehydrogenase 1, corn light harvesting complex, corn heat shock protein, pea small subunit RuBP carboxylase, mannopine synthase, nopaline synthase, petunia chalcone isomerase, bean glycine rich protein 1, potato patatin, or an S-E9 small subunit RuBP carboxylase promoter.

37. The host cell of claim 34 wherein said heterologous promoter is a bacterial expressible promoter.

38. The host cell of claim 34, wherein said heterologous promoter is a tac, trp, lac, T7, a lectin, glnA, sucA, CaMV35S, lac inducible, corn sucrose synthetase 1, corn alcohol dehydrogenase 1, corn light harvesting complex, corn heat shock protein, pea small subunit RuBP carboxylase, mannopine synthase, nopaline synthase, petunia chalcone isomerase, bean glycine rich protein 1, potato patatin, or an S-E9 small subunit RuBP carboxylase promoter.

39. The host cell of claim 34, wherein said gene is comprised within a vector.

40. The host cell of claim 34, wherein said gene comprises the sequence of SEQ ID NO: 1.

41. The host cell of claim 34, wherein said host cell is a prokaryotic host cell.

42. The host cell of claim 41, wherein said host cell is a cyanobacterial or bacterial host cell.

43. The host cell of claim 42, wherein said host cell is an *E. coli* or Agrobacterium sp. host cell.

44. The host cell of claim 43, wherein said host cell is an *Agrobacterium tumefaciens* host cell.

45. The host cell of claim 34, wherein said host cell is a eukaryotic host cell.

46. The host cell of claim 45, wherein said host cell is a plant host cell.

47. The host cell of claim 46 wherein said host cell is a monocotyledonous or dicotyledonous plant host cell.

48. The host cell of claim 47 wherein said host cell is a maize, rice, wheat, barley, oats, rye, asparagus, grain, cereal, sugar beet, soybean, alfalfa, fava bean, pea, bean, tomato, potato, tobacco, apple, cherry, pear, strawberry, raspberry, legume, tuber, or fruit plant host cell.

\* \* \* \* \*